United States Patent
Colter et al.

(10) Patent No.: US 10,413,571 B2
(45) Date of Patent: Sep. 17, 2019

(54) KIDNEY-DERIVED CELLS AND METHODS OF USE IN TISSUE REPAIR AND REGENERATION

(71) Applicant: DePuy Synthes Products, Inc., Raynham, MA (US)

(72) Inventors: David C. Colter, Hamilton, NJ (US); Agnieszka Seyda, North Brunswick, NJ (US); Charito S. Buensuceso, North Brunswick, NJ (US); Anna Gosiewska, Skillman, NJ (US)

(73) Assignee: DePuy Synthes Products, Inc., Raynham, MA (US)

(*) Notice: Subject to any disclaimer, the term of this patent is extended or adjusted under 35 U.S.C. 154(b) by 166 days.

(21) Appl. No.: 15/238,993

(22) Filed: Aug. 17, 2016

(65) Prior Publication Data

US 2016/0375062 A1    Dec. 29, 2016

Related U.S. Application Data

(62) Division of application No. 11/871,045, filed on Oct. 11, 2007.

(60) Provisional application No. 60/829,238, filed on Oct. 12, 2006.

(51) Int. Cl.
  *C12N 5/071* (2010.01)
  *A61K 35/22* (2015.01)
  *A61K 35/12* (2015.01)

(52) U.S. Cl.
  CPC ............ *A61K 35/22* (2013.01); *C12N 5/0686* (2013.01); *C12N 5/0687* (2013.01); *A61K 35/12* (2013.01); *C12N 2533/40* (2013.01)

(58) Field of Classification Search
  CPC .................................................. C12N 5/0686
  See application file for complete search history.

(56) References Cited

U.S. PATENT DOCUMENTS

| | | |
|---|---|---|
| 5,286,632 A | 2/1994 | Jones |
| 5,320,962 A | 6/1994 | Stiles et al. |
| 5,342,761 A | 8/1994 | MacLeod |
| 6,355,699 B1 | 3/2002 | Vyakarnam et al. |
| 6,458,588 B1 | 10/2002 | Arnaout et al. |
| 2002/0081725 A1 | 6/2002 | Tsang et al. |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0264269 A1 | 11/2007 | Harmon et al. |
| 2008/0112939 A1 | 5/2008 | Colter et al. |
| 2008/0145934 A1 | 6/2008 | Harris et al. |
| 2008/0166328 A1 | 7/2008 | Harmon et al. |
| 2010/0210013 A1 | 8/2010 | Mistry et al. |
| 2010/0215714 A1 | 8/2010 | Messina et al. |
| 2010/0260843 A1 | 10/2010 | Messina et al. |

FOREIGN PATENT DOCUMENTS

| | | |
|---|---|---|
| WO | WO-90/11354 A1 | 10/1990 |
| WO | WO-92/03917 A1 | 3/1992 |
| WO | WO-93/04169 A1 | 3/1993 |
| WO | WO-95/17911 A1 | 7/1995 |
| WO | WO-02/061053 A1 | 8/2002 |
| WO | WO-2005/021738 A1 | 3/2005 |
| WO | WO-08/045498 A1 | 4/2008 |

(Continued)

OTHER PUBLICATIONS

Parr et al. (2007, Bone Marrow Transplant, vol. 40, pp. 609-619) (Year: 2007).*
Li et al. (2010, J. Cerebral Blood Flow and Metabolism, vol. 30, pp. 653-662) (Year: 2010).*
Chute JP, 2006, Current Opin. Hematology, vol. 13, pp. 399-406 (Year: 2006).*
Schultz et al. (2007, Nature Rev. Immunology, vol. 7, pp. 118-130) (Year: 2007).*
In the U.S. Patent and Trademark Office, Non-Final Office Action in re; U.S. Appl. No. 11/871,045 dated Apr. 27, 2009, 7 pages.
In the U.S. Patent and Trademark Office, Non-Final Office Action in re; U.S. Appl. No. 11/871,045 dated Nov. 30, 2009, 8 pages.

(Continued)

*Primary Examiner* — Thaian N Ton
*Assistant Examiner* — David A. Montanari
(74) *Attorney, Agent, or Firm* — Baker & Hostetler LLP; Toni-Junell Herbert

(57) ABSTRACT

Isolated or purified mammalian kidney-derived cell populations from mammalian kidney tissue are provided. Methods are provided for the isolation and purification of the mammalian kidney-derived cell population. Methods for treating kidney disease are provided by administration of the isolated or purified mammalian kidney-derived cell population to a mammalian subject.

11 Claims, No Drawings

(56) References Cited

FOREIGN PATENT DOCUMENTS

WO    WO-08/045498    4/2009

OTHER PUBLICATIONS

In the U.S. Patent and Trademark Office, Final Office Action in re; U.S. Appl. No. 11/871,045 dated Jun. 3, 2010, 7 pages.
In the U.S. Patent and Trademark Office, Non-Final Office Action in re; U.S. Appl. No. 11/871,045 dated Mar. 6, 2014, 12 pages.
In the U.S. Patent and Trademark Office, Non-Final Office Action in re; U.S. Appl. No. 11/871,045 dated Oct. 17, 2014, 10 pages.
In the U.S. Patent and Trademark Office, Final Office Action in re; U.S. Appl. No. 11/871,045 dated May 7, 2015, 10 pages.
In the U.S. Patent and Trademark Office, Non-Final Office Action in re; U.S. Appl. No. 11/871,045 dated May 18, 2016, 15 pages.
Brodie et al., "Stem Cell Approaches for the Treatment of Renal Failure," *Pharmacological Reviews*, 2005, vol. 57(3), pp. 299-313.
Bussolati et al., "Isolation of Renal Progenitor Cells from Adult Human Kidney," *American Journal of Pathology*, 2005, vol. 166, No. 2, pp. 545-555.
Challen et al., "Identifying the Molecular Phenotype of Renal Progenitor Cells," *J. Am. Soc. Nephrol.*, 2004, vol. 15, pp. 2344-2357.
Gupta, S. et al., "Isolation and Characterization of Kidney-Derived Stem Cells," *J. Am. Soc. Nephrol.*, 2006, vol. 17(11), pp. 3028-3040.
Herrera et al., "Mesenchymal Stem Cells Contribute to the Renal Repair of Acute Tubular Epithelial Injury," *Int. J. Mol. Med.*, 2004, vol. 14(6), pp. 1035-1041.
Hill, D.P. and Wurst, W., "Screening for novel pattern formation genus using gene trap approaches," *Methods of Enzymology*, 1993: 225: pp. 664-681.
Hishikawa et al., "Musculin/MyoR is Expressed in Kidney Side Population Cells and can Regulate Their Function," *Journal of Cell Biology*, 2005, vol. 169(6), pp. 921-928.
Hoeben et al., "Vascular Endothelial Growth Factor and Angiogenesis," *Pharmacological Reviews*, 2004, vol. 56, pp. 549-580.
Karihaloo et al.,"Vascular Endothelial Growth Factor Induces Branching Morphogenesis/Tubulogenesis in Renal Epithelial Cells in a Neuropilin-Dependent Fashion," *Molecular and Cellular Biology*, 2005, vol. 25(17), pp. 7441-7448.
Kawamura et al., "Acetylation of GATA-4 is Involved in the Differentiation of Embryonic Stem Cells into Cardiac Myocytes," *Journal of Biological Chemistry*, 2005, vol. 280(20), pp. 19682-19688.
Kelly, K.J., and Molitoris, B.A., "Acute Renal Failure in the New Millennium: Time to Consider Combination Therapy," *Seminal Nephrol.*, 2000; 20(1): pp. 4-19.
Kitamura, S. et al., "Establishment and Characterization of Renal Progenitor Like Cells From S3 Segment of Nephron in Rat Adult Kidney," *The FASEB Journal*, 2005, vol. 19, pp. 1789-1797.
Klahr et al., "Obstructive Nephropathy and Renal Fibrosis," *Am. J. Renal Physiol.*, 2002, vol. 283(5), pp. F861-F875.
Laface et al., "Gene Transfer into Hematopoietic Progenitor Cells Mediated by an Adeno-Associated Virus Vector," *Virology*, 1988, vol. 162, pp. 483-486.
Maeshima, A. et al.,"Adult Kidney Tubular Cell population Showing Phenotypic Plasticity, Tubulogenic Capacity, and Integration Capability into Developing Kidney," *J. Am. Soc. Nephrol.*, 2006, vol. 17, pp. 188-198.
Markowicz et al., "Enhancing the Vascularization of Three-Dimensional Scaffolds: New Strategies in Tissue Regeneration and Tissue Engineering," *Topics in Tissue Engineering*, 2005, vol. 2, pp. 1-15.
Mombaerts et al., "Creation of a Large Genomic Deletion at the T-Cell Antigen Receptor β-Subunit Locus in Mouse Embryonic Stem Cells by Gene Targeting," *Proc. Nat. Acad. Sci.*, U.S.A., 1991, vol. 88, pp. 3084-3087.
Morgenstern et al., "Advanced Mammalian Gene Transfer: High Titre Retroviral Vectors with Multiple Drug Selection Markers and a Complementary Helper-Free Packaging Cell Line," *Nucleic Acids Res.*, 1990, vol. 18, pp. 3587-3596.
Morigi et al., "Mesenchymal Stem Cells are Renotropic, Helping to Repair the Kidney and Improve Function in Acute Renal Failure," *J. Am. Soc. Nephrol.*, 2004, vol. 15(7), pp. 1794-1804.
Ninichuk et al., "Multipotent Mesenchymal Stem Cells Reduce Interstitial Fibrosis but do no Delay Progression of Chronic Kidney Disease in Collagen4A3-Deficient Mice," *Kidney Int.*, 2006, vol. 70(1), pp. 121-129.
Oliver et al., "The Renal Papilla is a Niche for Adult Kidney Stem Cells," *Journal of Clinical Investigation*, 2004, vol. 114(6), pp. 795-804.
Sagrinati, C. et al., "Isolation and Characterization of Multipotent Progenitor Cells from the Bowman's Capsule of Adult Human Kidneys," *J. Am. Soc. Nephrol.*, 2006, vol. 17(9), pp. 2443-2456.
Stem Cells, Scientific Progress and Future Research Directions, Appendix E: Stem Cell Markers, National Institutes of Health, Bethesda, MD; 2001: pp. 1-12.
Studies Promoted by Daiwa Securities Health Foundation, Series 29, Mar. 1, 2006, pp. 12-16. [English Data Sheet Attached].
Wang, Y., et al., "Isolation and identification of human fetal kidney-derived mesenchymal-like stem cells and their differentiation into adipocyte and osteoblast," *Chinese Journal of Clinical Rehabilitation*, 2006; 25: pp. 17-20.
Yokoo, T. et al., "Stem Cell Gene Therapy for Chronic Renal Failure," *Curr. Gene Ther.*, 2003; 3: pp. 387-394.

* cited by examiner

KIDNEY-DERIVED CELLS AND METHODS OF USE IN TISSUE REPAIR AND REGENERATION

CROSS REFERENCE TO RELATED APPLICATION

This application is a divisional application of U.S. application Ser. No. 11/871,045, filed Oct. 11, 2007, published May 15, 2008 as U.S. Publication No. US 2008/0112939, which claims the benefit of U.S. Provisional Application No. 60/829,238, filed Oct. 12, 2006, the disclosures of each of which is hereby incorporated by reference in its entirety.

FIELD

The invention generally relates to isolated or purified mammalian kidney-derived cell populations from mammalian kidney tissue. The invention further relates to methods for the isolation and purification of the mammalian kidney-derived cell population. Methods for treating kidney disease are provided by administration of the isolated or purified kidney-derived cell populations to a mammalian subject.

BACKGROUND

Nephrotoxic and ischemic insults to the kidney lead to acute renal failure and most often manifest as acute tubular necrosis. Recovery of renal function after acute renal failure is dependent on the replacement of necrotic tubular cells with functional tubular epithelium. In addition, a pronounced proliferative response of the glomerular and peritubular capillary endothelium is observed after ischemic injury. The absence or reduction of epithelial and endothelial regeneration may predispose a patient to tubulointerstitial renal scarring and chronic renal disease. The origin of newly generated renal cells is primarily undefined, but by analogy to other organs, organ-specific pluripotent cells (i.e., renal stem cells) have been suggested as precursors of new cells. However, the identification of adult renal progenitor cells is lacking. Bussolati et al, *American J. of Pathology*, 166: 545-555, 2005.

Evidence is not conclusive to demonstrate the isolation and culture of renal progenitor cells. Nonetheless a few laboratories have made some attempts to identify and isolate such cells. For example, a study in rodents showed that the renal papilla is a niche for adult kidney stem cells. Further experimentation demonstrated that isolated renal papillary cells possess some degree of multipotential differentiation and when injected directly into the renal cortex, they engraft into the kidney parenchyma. These results suggest that the renal papilla is a niche for a population of kidney progenitor cells involved in kidney maintenance and repair. However, the existence of this progenitor niche in human kidneys remains to be determined. Oliver et al., *J. of Clinical Investigation*, 114: 795-804, 2004. PCT International Application No. WO2005/021738.

Putative human progenitor cells were isolated from renal tissue of cadaveric kidneys. Isolation of these cells was based on magnetic bead cell separation targeting the surface marker CD133. Further experimentation showed that renal-derived CD133+ cells have the capacity to expand in culture and differentiate in vitro into epithelial or endothelial cells. Upon implantation into SCID mice, CD133+ cells formed tubular structures that expressed renal epithelial markers. Additionally, intravenous injection into mice with glycerol-induced tubulonecrosis, CD133+ cells migrated and integrated into injured kidney tissue. Bussolati et al, *American J. of Pathology*, 166: 545-555, 2005. These data indicate that progenitor cells are present in human kidney tissue and they might play a role in renal repair. However, the resident population of CD133+ cells in adult kidney tissue is very low and therefore impractical for allogeneic-based cell therapy. A recent approach to identify organ-specific stem cells utilized isolation methods based on the ability of progenitor cells to efflux Hoechst 33342 dye. Cells demonstrating this ability have been termed SP (side-population) cells and have shown varying degrees of stem cell characteristics. Studies have shown that the renal interstitium of rodent kidneys contains SP cells. In addition, kidney SP cells were infused into mice with acute renal failure. Hishikawa et al., *J. of Cell Biology*, 169: 921-928, 2005. These cells appeared to migrate to the interstitial space and play a role in repair of the damaged renal tissue. However, the existence of SP cells in human kidney tissue remains to be determined. A need exists in the art for an improved source of mammalian or human kidney-derived cells for use in cellular therapy that can be isolated from normal mammalian or human kidney tissue and grown in cell culture.

SUMMARY

The present invention provides an isolated or purified mammalian kidney-derived cell population from mammalian kidney tissue. Methods for the isolation and purification of the mammalian kidney-derived cell population are provided. A unique population of mammalian kidney-derived cells is characterized by phenotypic characteristics, for example, morphology, growth potential, surface marker phenotype, early development gene expression and kidney development gene expression. Both surface marker and gene expression phenotype is retained after multiple passages of the mammalian kidney-derived cell population in culture.

In one aspect of the invention, an isolated or purified mammalian kidney-derived cell population is provided, said cell population capable of self-renewal and expansion in culture, wherein the cell population is positive for expression of at least one of Oct-4, Rex-1, Pax-2, Cadherin-11, FoxD1, WT1, Eya1, HNF3B, CXC-R4, Sox-17, EpoR, BMP2, BMP7, or GDF5 and negative for the expression of at least one of Sox2, FGF4, hTert, Wnt-4, SIX2 or GATA-4. In one embodiment, the cell is positive for expression of at least one of Eya1, WT1, FoxD1, BMP7, BMP2, GDF5, EpoR or Rex-1, and negative for expression of at least one of Sox2, FGF4, hTert or Wnt-4.

The isolated or purified mammalian kidney-derived cell population, in a further aspect, is positive for at least one of cell-surface markers HLA I, CD24, CD29, CD44, CD49c, CD73, CD166, or SSEA-4, and negative for at least one of cell-surface markers HLA II, CD31, CD34, CD45, CD56, CD80, CD86, CD104, CD105, CD117, CD133, CD138, CD141, or E-cadherin. In one embodiment, the cell population is positive for at least one of the surface markers HLA I, CD166 or SSEA-4, and negative for at least one of the cell-surface markers HLA II, CD80, CD86, CD133, CD141 or E-cadherin. In yet another embodiment, the cell population is positive for the cell-surface marker HLA I, and negative for at least one of cell-surface markers HLA II, CD80, or CD86. The cell population is preferably non-immunogenic for allogeneic transplantation in a mammalian subject. The mammalian kidney-derived cell population may secrete at least one of trophic factors FGF2, HGF, TGFα, TIMP-1, TIMP-2, MMP-2 or VEGF. Preferably, the cell population does not secrete at least one of trophic factors PDGF-bb or IL12p70.

The mammalian kidney-derived cell population may be derived from kidney subcapsular region, from kidney cortex, or from kidney medulla. The mammalian kidney-derived cell population may comprise kidney progenitor cells. The mammalian kidney-derived cell population may be derived from humans, primates, or rodents.

Another aspect of the invention relates to a method for treating ischemic kidney disease in a mammalian subject which comprises administering to the mammalian subject a therapeutically effective amount of an isolated or purified mammalian kidney-derived cell population as described above, thereby reducing or eliminating the ischemic kidney disease in the mammalian subject.

A method for replacing renal tissues, organs, components or structures which are damaged due to trauma, age, metabolic or toxic injury, disease or idiopathic loss in a mammalian subject is also provided. The method comprises administering to the mammalian subject a therapeutically effective amount of an isolated or purified mammalian kidney-derived cell population thereby reducing or eliminating the damaged tissues or organs and restoring kidney function in the mammalian subject.

A further aspect of the invention relates to a method for selectively enriching or isolating a mammalian kidney-derived cell population. This method comprises obtaining tissue from the subcapsular region, cortex, or medulla of a mammalian kidney, incubating the tissue in the presence of a metalloprotease, a neutral protease, or a mucolytic enzyme, plating the cells in a tissue culture vessel, identifying the cell population that is positive for expression of at least one of Oct-4, Rex-1, Pax-2, Cadherin-11, FoxD1, WT1, Eya1, HNF3B, CXC-R4, Sox-17, EpoR, BMP2, BMP7, or GDF5 and negative for the expression of at least one of Sox2, FGF4, hTert, Wnt-4, SIX2 or GATA-4 and isolating the mammalian kidney-derived cell population. The cell population, in a further aspect, is positive for at least one of cell-surface markers HLA I, CD24, CD29, CD44, CD49c, CD73, CD166, or SSEA-4, and negative for at least one of cell-surface markers HLA II, CD31, CD34, CD45, CD56, CD80, CD86, CD104, CD105, CD117, CD133, CD138, CD141, or E-cadherin.

A method for treating a disease in a mammalian subject with gene therapy is also provided, which comprises isolating a mammalian kidney-derived cell population derived from mammalian kidney tissue as described above, genetically altering the isolated or purified mammalian kidney-derived cell population to produce a therapeutic gene product, expanding the genetically altered cells in culture, and administering the genetically altered cells to produce the desired gene product in the mammalian subject and to reduce or eliminate the disease in the mammalian subject.

In a further aspect, a method for screening a potential drug candidate to treat a disorder involving renal cells in a mammalian subject is provided which comprises the steps of: (a) preparing an isolated or purified mammalian kidney-derived cell population derived from the mammalian kidney cells or kidney tissue from the patient, said cell capable of self-renewal and expansion in culture, wherein the cell population is positive for expression of at least one of Oct-4, Rex-1, Pax-2, Cadherin-11, FoxD1, WT1, Eya1, HNF3B, CXC-R4, Sox-17, EpoR, BMP2, BMP7, or GDF5 and negative for the expression of at least one of Sox2, FGF4, hTert, Wnt-4, SIX2 or GATA-4; (b) culturing the mammalian kidney-derived cell population under proliferation conditions to obtain a cellular composition comprising cells with potential or increased potential for self-renewal and expansion in vitro; (c) exposing the cultured cells in (a) or (b) to a potential drug candidate; and (d) detecting the presence or absence of an effect of the potential drug candidate on the survival of the cells, on a morphological, functional, or on a physiological characteristic and/or molecular biological property of said cells, whereby an effect altering a cell survival, a morphological, functional or physiological characteristic and/or a molecular biological property of the cells indicates the activity of the potential drug candidate. The cell population, in a further aspect, is positive for at least one of cell-surface markers HLA I, CD24, CD29, CD44, CD49c, CD73, CD166, or SSEA-4, and negative for at least one of cell-surface markers HLA II, CD31, CD34, CD45, CD56, CD80, CD86, CD104, CD105, CD117, CD133, CD138, CD141, or E-cadherin.

A method for assaying toxicity of a test substance to affect self-renewal and expansion in culture of an isolated or purified mammalian kidney-derived cell population is also provided. This method comprises the steps of: (a) culturing the isolated or purified mammalian kidney-derived cell population derived from mammalian kidney tissue, said cell capable of self-renewal and expansion in culture, wherein the cell population is positive for expression of at least one of Oct-4, Rex-1, Pax-2, Cadherin-11, FoxD1, WT1, Eya1, HNF3B, CXC-R4, Sox-17, EpoR, BMP2, BMP7, or GDF5 and negative for the expression of at least one of Sox2, FGF4, hTert, Wnt-4, SIX2 or GATA-4; (b) exposing the cultured cells in step (a) to test a substance; and (c) detecting the presence or absence of an effect of the test substance on the survival of the cells or on a morphological, functional, or physiological characteristic and/or molecular biological property of the cells, whereby an effect altering cell survival a morphological, functional, or physiological characteristic and/or a molecular biological property of the cells indicates the activity of the test substance. The cell population, in a further aspect, is positive for at least one of cell-surface markers HLA I, CD24, CD29, CD44, CD49c, CD73, CD166, or SSEA-4, and negative for at least one of cell-surface markers HLA II, CD31, CD34, CD45, CD56, CD80, CD86, CD104, CD105, CD117, CD133, CD138, CD141, or E-cadherin.

DETAILED DESCRIPTION

Overview

The present invention provides an isolated or purified mammalian kidney-derived cell population from mammalian kidney tissue. Methods for isolating and purifying cells from mammalian kidney tissue are provided. A unique population of mammalian kidney-derived cells is characterized by phenotypic characteristics, for example, morphology, growth potential, surface marker phenotype, kidney development gene expression, early development gene expression or renoprotective gene expression. Both surface marker and gene expression phenotypes are retained after multiple passages of the mammalian kidney-derived cell population in culture.

An isolated or purified mammalian kidney-derived cell population is provided, said cell population capable of self-renewal and expansion in culture, wherein the cell population is positive for expression of at least one of Oct-4, Rex-1, Pax-2, Cadherin-11, FoxD1, WT1, Eya1, HNF3B, CXC-R4, Sox-17, EpoR, BMP2, BMP7, or GDF5 and negative for the expression of at least one of Sox2, FGF4, hTert, Wnt-4, SIX2 or GATA-4. The isolated or purified mammalian kidney-derived cell population is stable and capable of self-renewal and expansion in cell culture. In one embodiment, the cell is positive for expression of at least one of Eya1, WT1, FoxD1, BMP7, BMP2, GDF5, EpoR or Rex-1, and negative for expression of at least one of Sox2, FGF4, hTert or Wnt-4. The cell population is non-immunogenic for allogeneic transplantation in a mammalian subject, as evidenced by the finding that the isolated or purified mammalian kidney-derived cell population is positive for the cell-surface marker HLA I, and negative for at least one of cell-surface markers HLA II, CD80, or CD86.

The mammalian kidney-derived cell population may secrete at least one of trophic factors FGF2, HGF, TGFα, TIMP-1, TIMP-2, MMP-2 or VEGF and does not secrete at least one of trophic factors PDGF-bb or IL12p70. The cell population can be derived from kidney subcapsular region, kidney cortex, or from kidney medulla, from a human, a primate, or a rodent. The mammalian kidney-derived cell population may include kidney progenitor cells. The kidney progenitor cells are capable of differentiating into distinct cell lineages, for example, adipocytes or osteoblasts.

The mammalian kidney-derived cell population of the present invention is useful in cell therapy for renal regeneration in ischemic kidney disease or for therapeutic treatments to replace kidney tissues, organs, components or structures which are damaged due to trauma, age, metabolic or toxic injury, disease or idiopathic loss in a mammalian subject.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Cells of the invention" refer to mammalian kidney-derived cell population and cells derived from them including differentiated or dedifferentiated cells. A mammalian kidney-derived cell population can be positive for expression of at least one of Oct-4, Rex-1, Pax-2, Cadherin-11, FoxD1, WT1, Eya1, HNF3B, CXC-R4, Sox-17, EpoR, BMP2, BMP7, or GDF5 and negative for the expression of at least one of Sox2, FGF4, hTert, Wnt-4, SIX2 or GATA-4.

"Differentiation" is the process by which an unspecialized ("uncommitted") or less specialized cell acquires the features of a specialized cell, such as a kidney cell, for example. A "differentiated or differentiation-induced cell" is one that has taken on a more specialized ("committed") position within the lineage of a cell. The term "committed," when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the "lineage" of a cell defines the heredity of the cell, i.e., which cells it came from and what cells it can give rise to. The lineage of a cell places the cell within a hereditary scheme of development and differentiation. A "lineage-specific marker" refers to a characteristic specifically associated with the phenotype of cells of a lineage of interest and can be used to assess the differentiation of an uncommitted cell to the lineage of interest.

In a broad sense, a "progenitor cell" is a cell that has the capacity to create progeny that are more differentiated than itself and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of "progenitor cell" may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a "non-renewing progenitor cell" or as an "intermediate progenitor" or "precursor cell". A differentiated cell can be derived from a multipotent cell which itself is derived from a multipotent cell, and so on. While each of these multipotent cells can be considered stem cells, the range of cell types each can give rise to may vary considerably. Some differentiated cells also have the capacity to give rise to cells of greater developmental potential. Such capacity can be natural or can be induced artificially upon treatment with various factors. "Proliferation" indicates an increase in cell number.

"Kidney progenitor cells" as used herein are mammalian kidney-derived cells that can give rise to cells, such as adipocytes, or osteoblasts or can give rise to one or more types of tissue, for example, renal tissue, in addition to producing daughter cells of equivalent potential. A "kidney or renal progenitor cell" is a multipotent or pluripotent cell that originates substantially from adult or fetal kidney tissue. These cells have been found to possess features characteristic of pluripotent stem cells, including rapid proliferation and the potential for differentiation into other cell lineages. "Multipotent" kidney progenitor cells can give rise to multiple cell lineages, e.g., renal cell lineages, adipocyte lineages, or osteoblast lineages. Kidney progenitor cells demonstrate a gene expression profile for early developmental gene markers, kidney developmental gene markers, metanephric mesenchymal gene markers, and genes that promote the survival of metanephric mesenchyme. For example, kidney progenitor cells demonstrate a gene expression profile which is positive for expression of genes including, but not limited to, Oct-4 and Rex-1, and negative for expression of genes including, but not limited to, Sox2, FGF4, hTERT and Wnt-4.

The isolated or purified mammalian kidney-derived cell population is stable and capable of self-renewal and expansion in cell culture. The mammalian kidney-derived cell population has been identified phenotypically as cells that are positive for expression of at least one of Oct-4, Rex-1, Pax-2, Cadherin-11, FoxD1, WT1, Eya1, HNF3B, CXC-R4, Sox-17, EpoR, BMP2, BMP7, or GDF5 and negative for the expression of at least one of Sox2, FGF4, hTert, Wnt-4, SIX2 or GATA-4. In a further aspect, the mammalian kidney-derived cell population has been identified as positive for expression of at least one of Eya1, WT1, FoxD1, BMP7, BMP2, GDF5, EpoR or Rex-1, and negative for expression of at least one of Sox2, FGF4, hTert or Wnt-4.

"Tissue" refers to a group or layer of similarly specialized cells, which together perform certain special functions. "Organ" refers to two or more adjacent layers of tissue, which layers of tissue maintain some form of cell-cell and/or cell-matrix interaction to form a microarchitecture.

"Kidney" refers to one of a pair of organs in the abdomen. Kidneys remove waste from the blood (as urine), produce erythropoietin to stimulate red blood cell production, and play a role in blood pressure regulation. Kidneys function to maintain proper water and electrolyte balance, regulate acid-base concentration, and filter the blood of metabolic wastes, which are then excreted as urine.

"Primary culture" refers to a mixed cell population of cells that permits interaction of many different cell types isolated from a tissue. The word "primary" takes its usual meaning in the art of tissue culture. "Capable of self-renewal and expansion in culture" refers to mammalian kidney-derived cell populations that grow and divide in cell culture and maintain substantially the same phenotype as measured by cell markers and secretion of trophic factors from mother cell to daughter cell. At some point during replication of the mammalian kidney-derived cell population, the phenotype can change to a more specialized or differentiated state of the kidney-derived cell.

The mammalian kidney-derived cell population of the invention can also be cultured prior to administration to a subject under conditions, which promote cell proliferation and differentiation. These conditions include culturing the cells to allow proliferation and confluence in vitro at which time the cells can be made to form aggregates or clusters and secret GDF5, BMP, or express BMP or EPO receptors.

Various terms are used to describe cells in culture. "Cell culture" refers generally to cells taken from a living organism and grown under controlled conditions, e.g., "in culture". A "primary cell culture" is a culture of cells, tissues or organs taken directly from organisms and before the first subculture. Cells are "expanded" in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as "doubling time."

"Cellular composition" refers to a preparation of cells, which preparation can include, in addition to the cells, non-cellular components such as cell culture media, e.g. proteins, amino acids, nucleic acids, nucleotides, co-enzyme, anti-oxidants, metals and the like. Furthermore, the cellular composition can have components which do not affect the growth or viability of the cellular component, but which are used to provide the cells in a particular format, e.g., as polymeric matrix for encapsulation or a pharmaceutical preparation.

"Culture medium" is recognized in the art and is also commonly known as "growth medium", generally refers to any substance or preparation used for the cultivation of living cells. Accordingly, a "tissue culture" refers to the maintenance or growth of tissue, e.g., explants of organ primordial, kidney subcapsular region, kidney cortex, or kidney medulla, or of an adult organ in vitro so as to preserve its architecture and function. A "cell culture" refers to growth of cells in vitro. Tissue and cell culture preparations of the amplified mammalian kidney-derived cell population can take on a variety of formats. For instance, a "suspension culture" refers to a culture in which cells multiply while suspended in a suitable medium. Likewise, a "continuous flow culture" refers to the cultivation of cells or explants in a continuous flow of fresh medium to maintain cell growth, e.g. viablity.

A "cell line" is a population of cells formed by one or more subcultivations of a primary cell culture. Each round of subculturing is referred to as a passage. When cells are subcultured, they are referred to as having been "passaged." A specific population of cells, or a cell line, is sometimes referred to or characterized by the number of times it has been passaged. For example, a cultured cell population that has been passaged ten times may be referred to as a "P10" culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is usually greater than the passage number. The expansion of cells (i.e., the number of population doublings) during the period between passaging depends on many factors, including, but not limited to the seeding density, substrate, medium, and time between passaging.

A "conditioned medium" is a medium in which a specific cell or population of cells has been cultured, and then removed. While the cells are cultured in the medium, they secrete cellular factors that can provide trophic support to other cells. Such trophic factors include, but are not limited to hormones, cytokines, extracellular matrix (ECM), proteins, antibodies, and granules. The medium containing the cellular factors is the conditioned medium.

Generally, a "trophic factor" is defined as a substance that promotes survival, growth, proliferation, maturation, differentiation, and/or maintenance of a cell, or stimulates increased activity of a cell. "Trophic support" is used herein to refer to the ability to promote survival, growth, proliferation, maturation, differentiation, and/or maintenance of a cell, or to stimulate increased activity of a cell. The mammalian kidney-derived cell population of the present invention produces trophic factors, including but not limited to, growth factors, cytokines, and differentiation factors. The trophic factors include, but are not limited to, FGF2, HGF, TGFα, TIMP-1, TIMP-2, VEGF, MMP-2, or a combination thereof.

"Non-immunogenic" refers to cells or a cell population that does not elicit a deleterious immune response in a majority of treated mammalian subjects, that is an immune response that compromises the mammalian subject's health or that interferes with a therapeutic response in the treated mammalian subject.

"Gene" refers to a nucleic acid sequence encoding a gene product. The gene optionally comprises sequence information required for expression of the gene (e.g., promoters, enhancers, etc.). The term "genomic" relates to the genome of an organism.

"Gene expression" refers to transcription of a gene into an RNA product, and optionally to translation into one or more polypeptide sequences.

"Gene expression data" refers to one or more sets of data that contain information regarding different aspects of gene expression. The data set optionally includes information regarding: the presence of target-transcripts in cell or cell-derived samples; the relative and absolute abundance levels of target transcripts; the ability of various treatments to induce expression of specific genes; and the ability of various treatments to change expression of specific genes to different levels.

"Gene expression profile" refers to a representation of the expression level of a plurality of genes without (i.e., baseline or control), or in response to, a selected expression condition (for example, incubation of the presence of a standard compound or test compound at one or several timepoints). Gene expression can be expressed in terms of an absolute quantity of mRNA transcribed for each gene, as a ratio of mRNA transcribed in a test cell as compared with a control cell, and the like. It also refers to the expression of an individual gene and of suites of individual genes in a subject.

When referring to cultured vertebrate cells, the term "senescence" (also "replicative senescence" or "cellular senescence") refers to a property attributable to finite cell cultures; namely, their inability to grow beyond a finite number of population doublings (sometimes referred to as "Hayflick's limit"). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their non-dividing state for as long as three years. These cells are very much alive and metabolically active, but they do not divide. The nondividing state of senescent cells has not yet been found to be reversible by any biological, chemical, or viral agent.

"Standard growth conditions" refers to standard atmospheric conditions comprising about 5% $CO_2$, a temperature of about 35-39° C., more preferably 37° C., and a relative humidity of about 100%.

"$ED_{50}$" means the dose of a drug which produces 50% of its maximum response or effect.

"Effective amount" refers to concentrations of components such as growth factors, cytokines, cells, preparations, or compositions effective for producing an intended result including proliferation of mammalian kidney-derived cells, or treating a disease or condition with cells, preparations, and compositions of the invention, or for effecting a transplantation of cells within a patient to be treated. An effective amount of components such as growth factors, cytokines, cells, preparations, or compositions brings about a change in the rate of cell proliferation and/or the state of differentiation of a cell.

"Administering" or "administration" refers to the process by which cells, preparations, or compositions of the invention are delivered to a patient for treatment purposes: Cells, preparations, or compositions can be administered a number of ways including parenteral (e.g. intravenous and intraarterial as well as other appropriate parenteral routes), oral, subcutaneous, inhalation, or transdermal. Cells, preparations, and compositions of the invention are administered in accordance with good medical practices taking into account the patient's clinical condition, the site and method of administration, dosage, patient age, sex, body weight, and other factors known to physicians.

"Animal" or "mammalian subject" refers to mammals, preferably mammals such as humans, primates, rats, or mice. Likewise, a "patient" or "subject" to be treated by the method of the invention can mean either a human or non-human animal, to whom treatment, including prophylactic treatment, with the cells, preparations, and compositions of the present invention, is provided. For treatment of those conditions or disease states that are specific for a specific animal such as a human patient, the term refers to that specific animal. A "donor" refers to an individual (animal including a human) who or which donates renal cells or kidney cells for use in a patient.

"Transplanting", "implanting", "transplantation", "grafting" and "graft" are used to describe the process by which cells, preparations, and compositions of the invention are delivered to the site within the patient where the cells are intended to exhibit a favorable effect, such as repairing damage to a patient's tissues, treating a disease, injury or trauma, or genetic damage or environmental insult to an organ or tissue caused by, for example an accident or other activity. Cells, preparations, and compositions can also be delivered in a remote area of the body by any mode of administration relying on cellular migration to the appropriate area in the body to effect transplantation.

"Explant" refers to a portion of an organ taken from the body and grown in an artificial medium.

"Ex vivo" refers to cells that have been taken from a body, temporarily cultured in vitro, and returned to a body.

"Essentially", "essentially effective", or "essentially pure" refers to a population of cells or a method which is at least 20+%, 30+%, 40+%, 50+%, 60+%, 70+%, 80+%, 85+%, 90+%, or 95+% effective, more preferably at least 98+% effective, most preferably 99+% effective. Therefore, a method that enriches for a given cell population, enriches at least about 20+%, 30+%, 40+%, 50+%, 60+%, 70+%, 80%, 85%, 90%, or 95% of the targeted cell population, most preferably at least about 98% of the cell population, most preferably about 99% of the cell population. In certain embodiments the cells in an enriched population of mammalian kidney-derived cell population of the invention comprised essentially of mammalian kidney-derived cells, for example, cells which are positive for expression of at least one of Eya1, WT1, FoxD1, BMP7, BMP2, GDF5, EpoR or Rex-1, and negative for expression of at least one of Sox2, FGF4, hTert or Wnt-4.

"Isolated" or "purified" refers to altered "by the hand of man" from the natural state i.e. anything that occurs in nature is defined as isolated when it has been removed from its original environment, or both. "Isolated" also defines a composition, for example, a mammalian kidney-derived cell population, that is separated from contaminants (i.e. substances that differ from the cell). In an aspect, a population or composition of cells is substantially free of cells and materials with which it may be associated in nature. "Isolated" or "purified" or "substantially pure", with respect to mammalian kidney-derived cells, refers to a population of mammalian kidney-derived cells that is at least about 50%, at least about 75%, preferably at least about 85%, more preferably at least about 90%, and most preferably at least about 95% pure, with respect to mammalian kidney-derived cells making up a total cell population. Recast, the term "substantially pure" refers to a population of mammalian kidney-derived cells of the present invention that contain fewer than about 50%, preferably fewer than about 30%, preferably fewer than about 20%, more preferably fewer than about 10%, most preferably fewer than about 5%, of lineage committed kidney cells in the original unamplified and isolated population prior to subsequent culturing and amplification. Purity of a population or composition of cells can be assessed by appropriate methods that are well known in the art.

"Gene therapy" refers to the transfer and stable insertion of new genetic information into cells for the therapeutic treatment of diseases or disorders. A variety of means for administering gene therapy to a mammalian subject will, in view of this specification, be apparent to those of skill in the art. Gene therapy techniques are described in the specification. A foreign gene is transferred into a cell that proliferates to introduce the transferred gene throughout the cell population. Therefore, cells and compositions of the invention can be the target of gene transfer, since they will produce various lineages, which will potentially express the foreign gene.

Mammalian kidney-derived cell population, or precursors thereof, generated in accordance with a method of the invention, can be used to treat kidney disorders, for example, ischemic kidney damage, renal failure, kidney transplantation, or renal cell carcinoma. The cells, or tissue or a functioning kidney tissue regenerated therefrom, can be administered to a patient to treat acute or chronic decline in renal function. Functional renal cells or regenerated renal tissue can be implanted into the donor of the kidney cells or into another patient. Renal cells or precursors thereof can also be used to construct an artificial kidney system, e.g., a system based on a hollow fiber filtration system.

The cells, cell preparations, and cellular compositions of the invention can be used as immunogens that are administered to a mammalian subject. Administration of a mammalian kidney-derived cell population obtained in accordance with the invention can be accomplished by various methods. Methods of administering cells as immunogens to a mammalian subject include without limitation immunization, administration to a membrane by direct contact (e.g. by swabbing or scratch apparatus), administration to mucous membranes (e.g. by aerosol), and oral administration Immunization can be passive or active and can occur via different routes including intraperitoneal injection, intradermal injection, and local injection. The route and schedule of immunization are in accordance with generally established conventional methods for antibody stimulation and production. Mammalian subjects, particularly mice, and antibody producing cells therefrom can be manipulated to serve as the basis for production of mammalian hybridoma cell lines.

The mammalian kidney-derived cell population compositions of the invention can be used to prepare model systems of disease. The mammalian kidney-derived cellular compositions of the invention can also be used to produce compounds including, but not limited to growth factors, hormones, cytokines, and immune-stimulating compounds.

The mammalian kidney-derived cell population of the present invention secretes factors including, but not limited to, FGF2, HGF, TGFα, TIMP-1, TIMP-2, VEGF, or MMP-2, or a combination thereof and does not secrete at least one of trophic factors PDGF-bb or IL12p70 or a combination thereof.

In an aspect, the invention provides a culture system from which genes, proteins, and other metabolites involved in proliferation or differentiation of mammalian kidney-derived cell populations or mammalian kidney progenitor cells can be identified and isolated. The cells in a culture system of the invention can be compared with other cells (e.g. differentiated cells) to determine the mechanisms and compounds that stimulate production of mammalian kidney-derived cells or mammalian kidney progenitor cells.

The cellular compositions of the invention can be used to screen for genes expressed in or essential for differentiation of mammalian kidney-derived cell population. Screening methods that can be used include Representational Difference Analysis (RDA) or gene trapping with, for example SA-lacZ. D. P. Hill and W. Wurst, 1993, *Methods in Enzymology*, 225: 664-681. Gene trapping can be used to induce dominant mutations (e.g., by deleting particular domains of the gene product) that affect differentiation or activity of mammalian kidney-derived cells and allow the identification of genes expressed in or essential for differentiation of these cells.

The expanded cell preparations of the invention comprising increased numbers of mammalian kidney-derived cells can be used for enhancing the immune system of a patient. The cell preparations will facilitate enhancement or reconstitution of the patient's immune and/or renal system. A mammalian kidney-derived cell population can be transfected with a vector to express immunogenic antigens, for example, viral, bacterial, parasite, or cancer antigens. This transfected mammalian kidney-derived cell population can be used to treat a mammalian subject suffering from a disease and thereby reduce or eliminate the viral, bacterial, parasitic disease, or reduce or eliminate the cancer or neoplastic disease.

The present invention further provides a method of treatment which uses mammalian kidney-derived cell populations to characterize cellular responses to biologic or pharmacologic agents involving isolating mammalian kidney-derived cells from a statistically significant population of individuals, culture expanding the mammalian kidney-derived cells from the statistically significant population of individuals to establish a plurality of cell cultures of mammalian kidney-derived cell populations, contacting the mammalian kidney-derived cell cultures with one or more biologic or pharmacologic agents, identifying one or more cellular responses to the one or more biologic or pharmacologic agents, and comparing the one or more cellular responses of the mammalian kidney-derived cell cultures from individuals in the statistically significant population.

The present invention also provides a method of treatment, which uses mammalian kidney-derived cells or specifically differentiated mammalian kidney-derived cell populations for therapy comprising administering the specifically differentiated cells to a patient. It further provides for the use of genetically engineered mammalian kidney-derived cells to selectively express an endogenous gene or a transgene, and for the use of mammalian kidney-derived cells grown in vivo for transplantation/administration into an animal to treat a disease. For example, differentiated cells derived from mammalian kidney-derived cell populations can be used to treat disorders involving tubular, vascular, interstitial, or glomerular structures of the kidney. For example, cells can be used to treat diseases of the glomerular basement membrane such as Alports Syndrome; tubular transport disorders such as Bartter syndrome, cystinuria or nephrogenic diabetes insipidus; progressive kidney diseases of varied etiologies such as diabetic nephropathy or glomerulonephritis; Fabry disease, hyperoxaluria, and to accelerate recovery from acute tubular necrosis.

Differentiated cells derived from a mammalian kidney-derived cell population can also be used to treat disorders such as acute kidney failure, acute nephritic syndrome, analgesic nephropathy, atheroembolic renal disease, chronic kidney failure, chronic nephritis, congenital nephrotic syndrome, end-stage renal disease, Goodpasture's syndrome, IgM mesangial proliferative glomerulonephritis, interstitial nephritis, kidney cancer, renal cancer, hypernephroma; adenocarcinoma of renal cells, kidney damage, kidney infection, kidney injury, kidney stones, lupus nephritis, membranoproliferative GN I, membranoproliferative GN II, membranous nephropathy, minimal change disease, necrotizing glomerulonephritis, nephroblastoma, nephrocalcinosis, nephrogenic diabetes insipidus, nephropathy-IgA, nephrosis (nephrotic syndrome), polycystic kidney disease, post-streptococcal GN, reflux nephropathy, renal artery embolism, renal artery stenosis, renal disorders, renal papillary necrosis, renal tubular acidosis type I, renal tubular acidosis type II, renal underperfusion, or renal vein thrombosis.

The mammalian kidney-derived cell population can be used to engraft a cell into a mammal comprising administering autologous, allogenic or xenogenic cells, to restore or correct tissue specific metabolic, enzymatic, structural or other function to the mammal. The cells can be used to engraft a cell into a mammal, causing the differentiation in vivo of cell types, and for administering the mammalian kidney-derived cells into the mammal. The cells, or their in vitro or in vivo differentiated progeny, can be used to correct a genetic disease, degenerative disease, or cancer disease process.

The mammalian kidney-derived cell population can be used as a therapeutic, for example, to aid in the recovery of a patient from chemotherapy or radiation therapy in the treatment of cancer, in the treatment of autoimmune disease, or to induce tolerance in the recipient.

The present invention further provides a method of gene profiling of a mammalian kidney-derived cell population, and the use of this gene profiling in a data bank. It also provides for the use of gene profiled mammalian kidney-derived cells in databases to aid in drug discovery.

The present invention further provides using mammalian kidney-derived cell populations or cells that were differentiated from mammalian kidney-derived cells in conjunction with a carrier device or scaffold to form an artificial kidney. Suitable carrier devices are well known in the art. For example, the carrier device can be a hollow, fiber-based device in use with the differentiated mammalian kidney-derived cell population. The invention further provides a method for removing toxins from the blood of a subject by contacting the blood ex vivo with isolated mammalian kidney-derived cell population which line a hollow, fiber-based device.

Additionally, in the methods described above, the cells can be administered in conjunction with an acceptable matrix, e.g., a pharmaceutically acceptable matrix. The matrix can be biodegradable. The matrix can also provide additional genetic material, cytokines, growth factors, or other factors to promote growth and differentiation of the cells. The cells can also be encapsulated prior to administration. The encapsulated cells can be contained within a polymer capsule.

The polymers used to prepare carrier devices, scaffolds, or matrices described herein are biodegradable and biocompatible. The biodegradable polymers readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment is retained by the body.

Examples of suitable biocompatible, bioabsorbable polymers that could be used include polymers selected from the group consisting of aliphatic polyesters, poly(amino acids), copoly(ether-esters), polyalkylene oxalates, polyamides, poly(iminocarbonates), polyorthoesters, polyoxaesters, polyamidoesters, polyoxaesters containing amine groups, poly(anhydrides), polyphosphazenes, biomolecules and blends thereof. For the purpose of this invention aliphatic polyesters include, but are not limited to homopolymers and copolymers of lactide (which includes lactic acid, d-, 1- and meso lactide), glycolide (including glycolic acid), epsilon-caprolactone, p-dioxanone (1,4-dioxan-2-one), trimethylene carbonate (1, 3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5, 8,12-tetraoxacyclotetradecane-7,14-dione), 1,5-dioxepan-2-one, 6,6-dimethyl-1, 4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof.

In one embodiment, polymers that are useful for the purposes of this invention are aliphatic polyesters which include, but are not limited to homopolymers and copolymers of lactide (which includes lactic acid, D-,L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5, 8,12-tetraoxacyclotetradecane-7,14-dione), 1,5-dioxepan-2-one, 6,6-dimethyl-1, 4-dioxan-2-one and polymer blends thereof. In another embodiment, natural polymers including, but not limited to collagen, gelatin, chitin, hyaluronic acid, elastin, fibronectin and the like are also suitable for the purposes of this invention. A combination of synthetic and natural polymers could also be used.

Another application of gene therapy permits the use of a drug in a high concentration, which is normally considered to be dangerous, by providing drug resistance to normal mammalian kidney-derived cells by transferring a drug resistant gene into the cells. In particular, it is possible to carry out the treatment using an anticancer drug in high concentration by transferring a gene having drug resistance against the anticancer drug, e.g., transferring a multiple drug resistant gene into an expanded cell preparation comprising mammalian kidney-derived cells.

Diseases other than those relating to the renal system can be treated by using the expanded cell preparations comprising mammalian kidney-derived cell populations in so far as the diseases relate to a deficiency of secretory proteins such as hormones, enzymes, cytokines, growth factors and the like. A deficient protein can be induced and expressed by transferring a gene encoding a target protein into the mammalian kidney-derived cell population under the control of a suitable promoter. The expression of the protein can be controlled to obtain the same activity as that obtained by the natural expression in vivo.

It is also possible to insert a gene encoding a ribozyme, an antisense nucleic acid or the like or another suitable gene into the mammalian kidney-derived cell population to control expression of a specific gene product in the cells or to inhibit susceptibility to diseases. For example, the mammalian kidney-derived cell population can be subjected to gene modification to express an antisense nucleic acid or a ribozyme, which can prevent growth of pathogens in the kidney including, but not limited to, HIV, HTLV-I, and HTLV-II.

The cell preparations comprising mammalian kidney-derived cell population can be introduced in a mammalian subject, who is a recipient of cell grafting, for example, by conventional intravenous administration.

The invention features a method for identifying agents, which influence the proliferation, differentiation, or survival of cells that have the potential to form mammalian kidney-derived cells. Examples of such agents are small molecules, antibodies, and extracellular proteins. Identified agents can be profiled and assessed for safety and efficacy in animals. In another aspect, the invention contemplates methods for influencing the proliferation, differentiation, or survival of cells that have the potential to form a mammalian kidney-derived cell population by contacting the cells with an agent or agents identified by the foregoing method. The identified agents can be formulated as a pharmaceutical preparation.

Genetic Engineering of a Mammalian Kidney-Derived Cell Population

The mammalian kidney-derived cell population of the invention can be engineered using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with DNA controlled by or in operative association with one or more appropriate expression control elements such as promoter or enhancer sequences, transcription terminators, polyadenylation sites, among others, and a selectable marker.

Following the introduction of the foreign DNA, engineered cells can be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines, which express the gene product.

Any promoter can be used to drive the expression of the inserted gene. For example, viral promoters include, but are not limited to, the CMV promoter/enhancer, SV40, papillomavirus, Epstein-Barr virus or elastin gene promoter. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary.

Inducible promoters include, but are not limited to, those associated with metallothionein and heat shock proteins. Examples of transcriptional control regions that exhibit tissue specificity have been described. For example, the erythropoietin promoter is specific for kidney tissues; high-capacity (type 2) $Na^+$/glucose cotransporter gene (Sglt2), a gene that is only expressed in early proximal tubules in kidney; and human organic anion transporter 3 (hOAT3/SLC22A8) is predominantly expressed in the proximal tubules of the kidney.

The cells of the invention can be genetically engineered to "knock out" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a mammalian kidney-derived cell can be reduced or knocked out using a number of techniques including, for example, inhibition of expression by inactivating the gene completely (commonly termed "knockout") using the homologous recombination technique. Usually, an exon encoding an important region of the protein is interrupted by a positive selectable marker, e.g., neo, preventing the production of normal mRNA from the target gene and resulting in inactivation of the gene. A gene can also be inactivated by creating a deletion in part of a gene, or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.* 88:3084).

Antisense, DNAzymes and ribozyme molecules, which inhibit expression of the target gene, can also be used in accordance with the invention to reduce the level of target gene activity. For example, antisense RNA molecules, which inhibit the expression of major histocompatibility gene complexes (HLA), have been shown to be most versatile with respect to immune responses. Antisense RNA molecules include, but are not limited to SiRNA oligonucleotides, or cDNA that produces SiRNA oligonucleotides. Still further, triple helix molecules can be utilized in reducing the level of target gene activity.

These techniques are described in detail by L. G. Davis et al. (eds), 1994, *Basic Methods in Molecular Biology*, 2nd ed., Appleton & Lange, Norwalk, Conn., which is incorporated herein by reference in its entirety.

Once the cells of the invention have been genetically engineered, they can be directly implanted into the patient to allow for the amelioration of the symptoms of renal disease by producing an anti-inflammatory gene product such as, for example, peptides or polypeptides corresponding to the idiotype of neutralizing antibodies for GM-CSF, TNF, IL-1, IL-2, or other inflammatory cytokines.

Alternatively, the genetically engineered cells can be used to produce new tissue in vitro, which is then implanted in the subject, as described supra.

Use of a Mammalian Kidney-Derived Cell Population for Transplantation

The treatment methods of the subject invention involve the implantation of a mammalian kidney-derived cell population, or trans-differentiated cells into individuals. The mammalian kidney-derived cell population of the present invention, for example, the cell population is positive for expression of at least one of Eya1, WT1, FoxD1, BMP7, BMP2, GDF5, EpoR or Rex-1, and negative for expression of at least one of Sox2, FGF4, hTert or Wnt-4, can be allogeneic or autologous, as evidenced by the finding that the cell population is positive for the cell-surface marker HLA I, and negative for at least one of cell-surface markers HLA II, CD80, or CD86, and can be delivered to the site of therapeutic need or "home" to the site. The cells of the present invention can differentiate in situ or provide trophic support to endogenous cells. The appropriate cell implantation dosage in humans can be determined from existing information relating to either the activity of the cells, for example GDF5 production, or the density of cells to treat kidney disease or ischemia. From in vitro culture and in vivo animal experiments, the amount of hormones produced can be quantified and used in calculating an appropriate dosage of implanted material. Additionally, the patient can be monitored to determine if additional implantation can be made or implanted material reduced accordingly.

To enhance the differentiation, survival or activity of implanted cells, additional factors can be added including growth factors such as morphogenetic proteins or corticosteroids, antioxidants or anti-inflammatory agents such as cyclosporin, statins, rapamycin, and p38 kinase inhibitors.

To enhance vascularization and survival of the transplanted cells angiogenic factors such as VEGF, PDGF or FGF2 can be added either alone or in combination with endothelial cells or their precursors including CD34+, CD34+/CD117+ cells, human umbilical tissue-derived cells, conditioned medium, extracellular matrix produced by cells or cell lysates.

Mammalian kidney-derived cell populations can be used to treat diseases or chronic conditions resulting in morbidity or reduced life expectancy. These conditions and diseases include, but are not limited to, acute renal failure, acute nephritic syndrome, analgesic nephropathy, atheroembolic renal disease, chronic kidney disease, chronic nephritis, congenital nephrotic syndrome, end-stage renal disease, Goodpasture's syndrome, IgM mesangial proliferative glomerulonephritis, interstitial nephritis, kidney cancer, renal cancer, hypernephroma; adenocarcinoma of renal cells, kidney damage, kidney infection, kidney injury, kidney stones, lupus nephritis, membranoproliferative GN I, membranoproliferative GN II, membranous nephropathy, minimal change disease, necrotizing glomerulonephritis, nephroblastoma, nephrocalcinosis, nephrogenic diabetes insipidus, diabetic retinopathy, nephropathy-IgA, nephrosis (nephrotic syndrome), polycystic kidney disease, post-streptococcal GN, reflux nephropathy, renal artery embolism, renal artery stenosis, renal disorders, renal papillary necrosis, renal tubular acidosis type I, renal tubular acidosis type II, renal underperfusion, or renal vein thrombosis. Clinical management strategies frequently focus on the prevention of further damage or injury rather than replacement or repair of the damaged tissue (e.g., renal tubules, glomeruli, neurons, glial cells, cardiac muscle). Clinical management strategies include treatment with exogenous steroids and synthetic, non-cellular pharmaceutical drugs, and have varying degrees of success, which can depend on the continued administration of the steroid or synthetic drug.

One or more other components can be added to transplanted cells, including selected extracellular matrix components, such as one or more types of collagen known in the art, and/or growth factors, platelet-rich plasma and drugs. Growth factors which can be usefully incorporated into the cell formulation include one or more tissue growth factors known in the art or to be identified in the future including, but not limited to BMPs, GDFs, IGF-I and -II, or growth hormone. Alternatively, the cells of the invention can be genetically engineered to express and produce trophic factors. Details on genetic engineering of the cells of the invention are provided in the disclosure and as known to those skilled in the art. Drugs which may be usefully incorporated into the cell formulation include anti-inflammatory compounds, pro-angiogenic compounds, anti-apoptotic compounds, as well as local anesthetics.

Encapsulation of a Mammalian Kidney-Derived Cell Population for Transplantation

A mammalian kidney-derived cell population, for example, the cell population is positive for expression of at least one of Eya1, WT1, FoxD1, BMP7, BMP2, GDF5, EpoR or Rex-1, and negative for expression of at least one of Sox2, FGF4, hTert or Wnt-4, can be allogeneic or autologous, as evidenced by the finding that the cell population is positive for the cell-surface marker HLA I, and negative for at least one of cell-surface markers HLA II, CD80, or CD86, may not be recognized by the immune system or may reduce the immune response as observed in the mixed-lymphocyte reaction.

It is preferred that the differentiated cells be derived from the patient that is being treated so as to avoid immune rejection. However, where autologous cells are not available, it can be useful to encapsulate the differentiated cells in a capsule that is permeable to nutrients and oxygen required by the cell and therapeutic factors the cell is secreting such as hormones or BMP-7, GDF5, yet impermeable to immune humoral factors and cells. Preferably the encapsulant is hypoallergenic, is easily and stably situated in a target tissue, and provides added protection to the implanted structure.

Protection from immune rejection can also be provided by genetic modification of the differentiated cells, according to any method known in the art. Autoantibody and CTL resistant cells can be produced using methods such as those disclosed in U.S. Pat. Nos. 5,286,632, 5,320,962, 5,342,761; and in WO 90/11354, WO 92/03917, WO 93/04169, and WO 95/17911. Alternatively, selection of resistant trans-differentiated cells is accomplished by culturing these cells in the presence of autoantibody or IDD associated CTLs or CTLs activated with IDD specific autoantigens. As a result of these techniques, cells having increased resistance to destruction by antibody or T-lymphocyte dependent mechanisms are generated. Such cells can be implanted into an appropriate host in an appropriate tissue as disclosed herein and have increased resistance to destruction by autoimmune processes.

Likewise, the human leukocyte antigen (HLA) profile of the differentiated cell can be modified, optionally by an iterative process, in which the differentiated cell is exposed to normal, allogeneic lymphocytes, and surviving cells selected. Alternatively, a site directed mutagenesis approach is used to eliminate the HLA markers from the surface of the differentiated cells, and modified differentiated cells thereby generated are implanted into a recipient mammal in need of such implantation.

In a specific example, the adeno-associated virus (AAV) vector system carrying the neomycin-resistance gene, neo, is used. AAV can be used to transfect eukaryotic cells (Laface et al. (1988) *Virology* 162:483). In addition, the pBABE-bleo shuttle vector system carrying the phleomycin-resistance gene is used (Morgenstein et al. (1990) *Nucleic Acids Res.* 18:3587). This shuttle vector can be used to transform human cells with useful genes as described herein.

Cryopreservation and Banking a Mammalian Kidney-Derived Cell Population

A mammalian kidney-derived cell population of the invention can be cryopreserved and maintained or stored in a "cell bank". Cryopreservation of cells of the invention can be carried out according to known methods. For example, but not by way of limitation, cells can be suspended in a "freeze medium" such as, culture medium further comprising 0 to 95 percent FBS and 0 to 10 percent dimethylsulfoxide (DMSO), a cryoprotectant, with or without 5 to 10 percent glycerol, at a density, for example, of about 0.5 to $10\times10^6$ cells per milliliter. Alternatively, other cryoprotectants may be used such as, carbohydrates including, but not limited to glucose, sucrose, maltose, and trehalose. The cells are dispensed into glass or plastic ampoules or other vessels that are then sealed and transferred to the freezing chamber of a controlled rate freezer. The optimal rate of freezing can be determined empirically. A programmable rate freezer for example, can give a change in temperature of $-1$ to $-10°$ C. per minute through the heat of fusion can be used. Once the ampoules have reached $-180°$ C., they are transferred to a liquid nitrogen storage area. Cryopreserved cells can be stored for a period of years, though they should be checked at least every 5 years for maintenance of viability.

The cryopreserved cells of the invention constitute a bank of cells, portions of which can be "withdrawn" by thawing and then used as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as DMEM conditioned with 10 percent FBS.

Use of a Mammalian Kidney-Derived Cell Population for In Vitro Screening of Drug Efficacy or Toxicity The mammalian kidney-derived cell population of the invention can be used in vitro to screen a wide variety of compounds for effectiveness and cytotoxicity of pharmaceutical agents, growth/regulatory factors, and anti-inflammatory agents. To this end, the cells of the invention, or tissue cultures described above, are maintained in vitro and exposed to the compound to be tested. The activity of a cytotoxic compound can be measured by its ability to damage or kill cells in culture. This can readily be assessed by vital staining techniques. The effect of growth/regulatory factors can be assessed by analyzing the number of living cells in vitro, e.g., by total cell counts, and differential cell counts. This can be accomplished using standard cytological and/or histological techniques, including the use of immunocytochemical techniques employing antibodies that define type-specific cellular antigens. The effect of various drugs on the cells of the invention either in suspension culture or in the three-dimensional system described above can be assessed.

The cells and tissues of the invention can be used as model systems for the study of physiological or pathological conditions. For example, the mammalian kidney-derived cell population of the present invention can be used to study disease states, for example, acute kidney failure, chronic kidney failure, kidney cancer, renal cancer, hypernephroma, adenocarcinoma of renal cells, kidney damage, kidney infection, kidney injury, kidney stones, lupus nephritis, polycystic kidney disease, or renal vein thrombosis.

The cells and tissues of the invention can also be used to study the mechanism of action of cytokines, growth factors, e.g., EPO, and inflammatory mediators, e.g., IL-1, TNF and prostaglandins. In addition, cytotoxic and/or pharmaceutical agents can be screened for those that are most efficacious for a particular patient, such as those that reverse, reduce or prevent kidney disease or kidney ischemia, or otherwise enhance the balanced growth of kidney tissue. Agents that prove to be efficacious in vitro could then be used to treat the patient therapeutically.

Use of a Mammalian Kidney-Derived Cell Population to Produce Biological Molecules In a further embodiment, the mammalian kidney-derived cell population of the invention can be cultured in vitro to produce biological products in high yield. For example, such cells, which either naturally produce a particular biological product of interest (e.g., a growth factor, regulatory factor, or peptide hormone), or have been genetically engineered to produce a biological product, could be clonally expanded using, for example, a three-dimensional cell culture system. If the cells excrete the biological product into the nutrient medium, the product can be readily isolated from the spent or conditioned medium using standard separation techniques, e.g., such as differential protein precipitation, ion-exchange chromatography, gel filtration chromatography, electrophoresis, and HPLC, to name but a few. A "bioreactor" can be used to take advantage of the flow method for feeding, for example, a three-dimensional culture in vitro. Essentially, as fresh media is passed through the three-dimensional culture, the biological product is washed out of the culture and can then be isolated from the outflow, as above.

Alternatively, a biological product of interest can remain within the cell and, thus, its collection can require that the cells are lysed. The biological product can then be purified using any one or more of the above-listed techniques.

Methods of Administration

In the methods described herein, the therapeutically effective amount of the mammalian kidney-derived cell population, for example, cells that are positive for expression of at least one of Eya1, WT1, FoxD1, BMP7, BMP2, GDF5, EpoR or Rex-1, and negative for expression of at least one of Sox2, FGF4, hTert or Wnt-4, can range from the maximum number of cells that is safely received by the subject to the minimum number of cells necessary for either induction of new blood vessel formation in the ischemic kidney tissue or for increasing blood flow to the ischemic kidney tissue, or to repair or regenerate kidney subcapsular region, kidney cortex, or kidney medulla tissue. Generally, the therapeutically effective amount of a mammalian kidney-derived cell population is at least $1\times10^4$ per kg of body weight of the subject and, most generally, need not be more than $1\times10^7$ of each type of cell per kg. Although it is preferable that the mammalian kidney-derived cell population is autologous or HLA-compatible with the subject, the mammalian kidney-derived cell population can be isolated from other individuals or species or from genetically-engineered inbred donor strains, or from in vitro cell cultures. The isolated or purified mammalian kidney-derived cell population is positive for cell-surface markers, HLA I, and negative for cell-surface markers, HLA II, CD80, or CD86. The cell population is non-immunogenic for allogeneic transplantation in a mammalian subject.

The therapeutically effective amount of the mammalian kidney-derived cell population can be suspended in a pharmaceutically acceptable carrier or excipient. Such a carrier includes, but is not limited to basal culture medium plus 1% serum albumin, saline, buffered saline, dextrose, water, collagen, alginate, hyaluronic acid, fibrin glue, polyethyleneglycol, polyvinylalcohol, carboxymethylcellulose and combinations thereof. The formulation should suit the mode of administration. Accordingly, the invention provides a use of human kidney tissue producing human kidney-derived cell population, for example, cells that are positive for expression of at least one of Eya1, WT1, FoxD1, BMP7, BMP2, GDF5, EpoR or Rex-1, and negative for expression of at least one of Sox2, FGF4, hTert or Wnt-4, for the manufacture of a medicament to treat an ischemic renal tissue in a subject. In some embodiments, the medicament further comprises recombinant polypeptides, such as growth factors, chemokines or cytokines. In further embodiments, the medicaments comprise a human kidney-derived cell population. The cells used to manufacture the medicaments can be isolated, derived, or enriched using any of the variations provided for the methods described herein.

The mammalian kidney-derived cell preparation or composition is formulated in accordance with routine procedures as a pharmaceutical composition adapted for intravenous administration to human beings. Typically, compositions for intravenous administration, intra-arterial administration or administration within the kidney capsule, are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Pharmaceutically acceptable carriers are determined in part by the particular composition being administered, as well as by the particular method used to administer the composition. Accordingly, there are a wide variety of suitable formulations of pharmaceutical compositions (see, e.g., Alfonso R Gennaro (ed), Remington: *The Science and Practice of Pharmacy*, formerly Remington's Pharmaceutical Sciences 20th ed., Lippincott, Williams & Wilkins, 2003, incorporated herein by reference in its entirety). The pharmaceutical compositions are generally formulated as sterile, substantially isotonic and in full compliance with all Good Manufacturing Practice (GMP) regulations of the U.S. Food and Drug Administration.

A variety of means for administering cells to subjects will, in view of this specification, be apparent to those of skill in the art. Such methods include injection of the cells into a target site in a subject. Cells can be inserted into a delivery device, which facilitates introduction by injection or implantation into the subjects. Such delivery devices can include tubes, e.g., catheters, for injecting cells and fluids into the body of a recipient subject. In a preferred embodiment, the tubes additionally have a needle, e.g., a syringe, through which the cells of the invention can be introduced into the subject at a desired location. In a preferred embodiment, mammalian kidney-derived cell populations are formulated for administration into a blood vessel via a catheter (where the term "catheter" is intended to include any of the various tube-like systems for delivery of substances to a blood vessel). Alternatively, the cells can be inserted into or onto a scaffold, including but not limited to textiles, such as weaves, knits, braids, meshes, and non-wovens, perforated films, sponges and foams, and beads, such as solid or porous beads, microparticles, nanoparticles, and the like. The cells can be prepared for delivery in a variety of different forms. For example, the cells can be suspended in a solution or gel. Cells can be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Modes of administration of the mammalian kidney-derived cell population, for example, cells that are positive for expression of at least one of Eya1, WT1, FoxD1, BMP7, BMP2, GDF5, EpoR or Rex-1, and negative for expression of at least one of Sox2, FGF4, hTert or Wnt-4, include but are not limited to systemic, intra-renal, intravenous or intra-arterial injection and injection directly into the tissue at the intended site of activity. The preparation can be administered by any convenient route, for example by infusion or bolus injection and can be administered together with other biologically active agents. Administration is preferably systemic. Most preferably, the site of administration is close to or nearest the intended site of activity. In cases when a subject suffers from global ischemia, a systemic administration, such as intravenous administration, is preferred. Without intending to be bound by mechanism, the composition comprising a mammalian kidney-derived cell population will, when administered, migrate or home to ischemic tissue, for example, in the kidney, in response to chemotactic factors produced due to the injury. Ischemic tissue that can be treated by the methods of the invention includes, but is not limited to, renal ischemia.

The methods described herein, provide a recombinant polypeptide or a drug is administered to the subject in combination with the administration of cells. The polypeptide or drug can be administered to the subject before, concurrently, or after the administration of the cells. In one preferred embodiment, the recombinant polypeptide or drug promotes angiogenesis, vasculogenesis, or both. In another embodiment, the recombinant polypeptide or drug promotes the proliferation or differentiation of the mammalian kidney-derived cell population. In one embodiment, the recombinant polypeptide is VEGF, FGF2, SDF, CXCR-4 or CXCR-5, or a fragment thereof, which retains a therapeutic activity to the ischemic tissue.

In particular, the invention methods are useful for therapeutic vasculogenesis for the treatment of renal ischemia in humans. Administration of a mammalian kidney-derived cell population, for example, cells are positive for expression of at least one of Eya1, WT1, FoxD1, BMP7, BMP2, GDF5, EpoR or Rex-1, and negative for expression of at least one of Sox2, FGF4, hTert or Wnt-4, according to invention methods can be used as a sole treatment or as an adjunct to surgical and/or medical treatment modalities. For example, the methods described herein for treatment of renal ischemia can be used in conjunction with treatment for kidney cancer, kidney infection, kidney damage, kidney transplantation, or kidney stones. The methods described herein are particularly useful for subjects that have incomplete revascularization of the ischemic area after surgical treatments and, therefore, have areas of ischemic but viable kidney tissue. Subjects that can significantly benefit from the therapeutic vasculogenesis according to the methods of the invention are those who have large areas of viable kidney tissue jeopardized by the impaired perfusion supplied by vessels that are poor targets for revascularization techniques.

The therapeutically effective amount of the mammalian kidney-derived cell population, for example, cells that are positive for expression of at least one of Eya1, WT1, FoxD1, BMP7, BMP2, GDF5, EpoR or Rex-1, and negative for expression of at least one of Sox2, FGF4, hTert or Wnt-4, is a maximum number of cells that is safely received by the subject. Because the preferred injection route is intra-renal, the maximum dose should take into consideration the size of the vessels into which the cells are infused, so that the vessels do not become congested or plugged. The minimum number of cells necessary for induction of new blood vessel formation in the ischemic renal tissue can be determined empirically, without undue experimentation, by dose escalation studies. For example, such a dose escalation could begin with approximately $10^4$ mammalian kidney-derived cells per kg body weight.

One aspect of the invention further provides a pharmaceutical formulation, comprising: (a) mammalian kidney-derived cell population, for example, cells that are positive for expression of at least one of Eya1, WT1, FoxD1, BMP7, BMP2, GDF5, EpoR or Rex-1, and negative for expression of at least one of Sox2, FGF4, hTert or Wnt-4, and a pharmaceutically acceptable carrier. In some embodiments, the formulation comprises from $10^4$ to $10^9$ mammalian kidney-derived cells. In a further embodiment, the formulation is prepared for administration by a catheter.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, *Molecular Cloning: A Laboratory Manual*, 3rd Ed., ed. by Sambrook and Russell (Cold Spring Harbor Laboratory Press: 2001); the treatise, *Methods In Enzymology* (Academic Press, Inc., N.Y.); *Using Antibodies*, Second Edition by Harlow and Lane, Cold Spring Harbor Press, New York, 1999; *Current Protocols in Cell Biology*, ed. by Bonifacino, Dasso, Lippincott-Schwartz, Harford, and Yamada, John Wiley and Sons, Inc., New York, 1999

Other embodiments and uses will be apparent to one skilled in the art in light of the present disclosures.

EXEMPLARY EMBODIMENTS

Example 1

Isolation of Human Kidney-Derived Cells

Normal human kidneys were obtained from the National Disease Research Interchange (NDRI, Philadelphia, Pa.). Each kidney was washed in Dulbecco's modified Eagles medium (DMEM-low glucose, Invitrogen, Carlsbad, Calif.) or phosphate buffered saline (PBS, Invitrogen) in order to remove blood and debris. Tissue was dissected from the outer cortex region, inner medullar region, and subcapsular region of the kidney. The tissues were then mechanically dissociated in tissue culture plates until the tissue was minced to a fine pulp. The tissue was then transferred to a 50-milliliter conical tube. The tissue was then digested in either good manufacturing practice (GMP) enzyme mixtures containing 0.25 units PZ activity/milliliter collagenase (NB6, N0002779, Serva Electrophoresis GmbH, Heidelberg, Germany), 2.5 units/milliliter dispase (Dispase II 165 859, Roche Diagnositics Corporation, Indianapolis, Ind.), 1 unit/milliliter hyaluronidase (Vitrase, ISTA Pharmaceuticals, Irvine, Ca) or non-GMP grade enzyme mixtures containing 500 units/milliliter collagenase (Sigma, St Louis, Mo.), 50 units/milliliter dispase (Invitrogen) and 5 units/milliliter hyaluronidase (Sigma). Kidney-derived cells were also isolated with 50 units/milliliter dispase. The enzyme mixture was combined with either renal epithelial growth medium (REGM) (Cambrex, Walkersville, Md.) or mesenchymal stem cell growth medium (MSCGM) (Cambrex). The conical tubes containing the tissue, medium and digestion enzymes were incubated at 37° C. in an orbital shaker at 225 rpm for 1 hour.

The digest was centrifuged at 150×g for 5 minutes and the supernatant was aspirated. The resulting cell pellet was resuspended in 20 milliliters of REGM or MSCGM. The cell suspension was filtered through a 40-micron nylon BD FALCON cell strainer (BD Biosciences, San Jose, Calif.). The filtrate was resuspended in medium (total volume 50 milliliters) and centrifuged at 150×g for 5 minutes. The supernatant was aspirated and the cell pellet was resuspended in 50 milliliters of fresh culture medium. This process was repeated twice more.

After the final centrifugation, the supernatant was aspirated and the cell pellet was resuspended in 5 milliliters of fresh culture medium. The number of viable cells was determined using a Guava instrument (Guava Technologies, Hayward, Calif.). Cells were then plated at a seeding density of 5000 cells/cm² onto 2% gelatin or laminin coated tissue culture flasks and cultured either in a low oxygen (hypoxia) or normal (normoxia) atmosphere. Table 1 shows the donor information and growth conditions used to isolate populations of kidney-derived cells. To obtain single-cell derived clones of kidney cells, limiting dilution techniques were performed. In total, cells were isolated using twenty-four different conditions, from four different cadaveric donors ages 39, 46, 21 and 10 years old.

Example 2

Kidney-Derived Cell Morphology

Seven days after isolation, kidney-derived cell populations were assessed by light microscopy and morphological characteristics of the cells were observed. Consistently, all isolation conditions gave rise to cells with an epithelial morphology. (Table 1).

TABLE 1

Conditions used to establish cultures of kidney-derived cells. Non-GMP grade enzymes (A). GMP-grade enzymes (B). Dispase (C). Age of donor in years (Age). Atmosphere cultures were grown (Atm). Normoxia (N) Hypoxia (H).

| Isolation | Age | Donor gender | Tissue source | Enzymes | Media | Substrate | Atm | Morphology |
|---|---|---|---|---|---|---|---|---|
| 1 | 39 | Male | Cortex | A | REGM | Gelatin | N | Epithelial |
| 2 | 39 | Male | Medulla | A | REGM | Gelatin | N | Epithelial |
| 3 | 39 | Male | Cortex | A | MSCGM | Gelatin | N | Epithelial |
| 4 | 39 | Male | Medulla | A | MSCGM | Gelatin | N | Epithelial |
| 5 | 39 | Male | Cortex | A | REGM | Gelatin | H | Epithelial |
| 6 | 39 | Male | Medulla | A | REGM | Gelatin | H | Epithelial |
| 7 | 39 | Male | Cortex | A | MSCGM | Gelatin | H | Epithelial |
| 8 | 39 | Male | Medulla | A | MSCGM | Gelatin | H | Epithelial |
| 9 | 39 | Male | Cortex | A | REGM | Laminin | N | Epithelial |
| 10 | 39 | Male | Medulla | A | REGM | Laminin | N | Epithelial |
| 11 | 39 | Male | Cortex | A | MSCGM | Laminin | N | Epithelial |
| 12 | 39 | Male | Medulla | A | MSCGM | Laminin | N | Epithelial |
| 13 | 39 | Male | Cortex | A | REGM | Laminin | H | Epithelial |
| 14 | 39 | Male | Medulla | A | REGM | Laminin | H | Epithelial |
| 15 | 39 | Male | Cortex | A | MSCGM | Laminin | H | Epithelial |
| 16 | 39 | Male | Medulla | A | MSCGM | Laminin | H | Epithelial |
| 17 | 46 | Male | Subcapsular | B | REGM | Gelatin | N | Epithelial |
| 18 | 46 | Male | Cortex | B | REGM | Gelatin | N | Epithelial |
| 19 | 46 | Male | Cortex | A | REGM | Gelatin | N | Epithelial |
| 20 | 46 | Male | Medulla | B | REGM | Gelatin | N | Epithelial |
| 21 | 46 | Male | Medulla | A | REGM | Gelatin | N | Epithelial |
| 22 | 21 | Male | Subcapsular | A | REGM | Gelatin | N | Epithelial |
| 23 | 21 | Male | Cortex | A | REGM | Gelatin | N | Epithelial |
| 24 | 10 | Female | Cortex | C | REGM | Gelatin | N | Epithelial |

This data illustrates that kidney-derived cells can be isolated from a donor of any age or gender, as well as isolated using various growth media formulations or culture conditions. The ease and consistency of the isolation procedure shows that kidney-derived cells are a valuable source of cells for use in cell-based therapies.

Example 3

Kidney-Derived Cell Growth Potential

Kidney-derived cells can be extensively propagated in culture and are able to generate significant numbers of cells in a short time. This is a criterion for the development of allogeneic cell therapies.

Kidney-derived cells were plated at 5,000 cells/cm² onto T75 flasks in REGM or MSCGM and cultured at 37° C. in 5% carbon dioxide. Cells were passaged every 2-5 days. At each passage, cells were counted and viability was measured using a Guava instrument (Guava Technologies, Hayward, Calif.). Cell populations were continually passaged for several weeks until senescence was reached. Senescence was determined when cells failed to achieve greater than one population doubling during the study time interval. Population doublings [ln(final cell yield/initial number of cells plated)/ln 2] were then calculated.

For karyotype analysis, passage 4 and passage 10 kidney-derived cells, from isolations 22 and 23, were plated into T25 flasks and allowed to attach overnight. Flasks were then filled with REGM and karyotype analysis was performed.

Table 2 is a summary of the growth data for isolations tested. There was no noticeable effect on the cell growth characteristics with regards to donor age, tissue source, or enzymes used to isolate the cells.

Karyotype analysis was performed on isolations 22 and 23 at both passage 4 and passage 10. Both demonstrated a normal karyotype at passage 4 and passage 10.

TABLE 2

Summary of growth potential data. Population doublings (PD). Refer to Table 1 for isolation number cross-reference.

| Isolation | Days until senescence | Passage | PD | Viability (%) |
|---|---|---|---|---|
| 1 | 54 | 12 | 31.2 | 98 |
| 2 | 54 | 12 | 26.8 | 98 |
| 17 | 51 | 11 | 30.2 | 98 |
| 18 | 48 | 10 | 26.8 | 97 |
| 19 | 42 | 9 | 24.9 | 97 |
| 20 | 48 | 10 | 31.0 | 98 |
| 21 | 48 | 10 | 29.0 | 98 |
| 22 | 47 | 16 | 28.7 | 97 |
| 23 | 47 | 16 | 27.9 | 97 |

On average, population doublings (PD) at senescence was 28.5, while the average viability was 97.6%.

In summary, kidney-derived cells have a robust growth potential in culture. These data can be used to estimate the total number of cells generated from one whole human kidney. If all of the kidney tissue was processed, and the resulting cells were cultured for 31 population doublings, one whole human kidney would yield an estimated $1.89 \times 10^{16}$ total cells. Therefore, considering that one therapeutic dose of cells is $1 \times 10^8$ cells per person, kidney-derived cells, isolated from a single kidney will be sufficient to treat 189 million patients. Ultimately, these cells are a highly expandable source of cells for use in allogeneic-based cell therapies.

Example 4

Kidney-Derived Cell Surface Marker Phenotype

Flow cytometric analysis was performed on kidney-derived cells to determine the surface marker phenotype. Cells from 9 of the isolations in Example 1 were expanded to passage 4 and passage 10 in REGM on T75 flasks at 37° C. and 5% carbon dioxide. Adherent cells were washed in PBS and detached with TrypLE Select (Gibco, Grand Island, N.Y.). Cells were harvested, centrifuged and resuspended in 3% (v/v) FBS in PBS at a concentration of $2 \times 10^5$ cells/milliliter. The specific antibody was added to 100 microliters of cell suspension and the mixture was incubated in the dark for 30-45 minutes at 4° C. After incubation, cells were washed with PBS and centrifuged to remove excess antibody. Cells were resuspended in 500 microliters PBS and analyzed by flow cytometry. Flow cytometry analysis was performed with a Guava Instrument (Guava Technologies, Hayward, Calif.). Antibodies used to characterize the surface marker phenotype are shown in Table 3.

TABLE 3

Antibodies used in characterizing cell the surface marker phenotype of kidney-derived cells.

| Antibody | Manufacture | Catalog number |
|---|---|---|
| CD34 | BD Pharmingen | 555821 |
| CD44 | BD Pharmingen | 555478 |
| CD45R | BD Pharmingen | 555489 |
| CD117 | BD Pharmingen | 340529 |
| CD141 | BD Pharmingen | 559781 |
| CD31 | BD Pharmingen | 555446 |
| CD49c | BD Pharmingen | 556025 |
| CD73 | BD Pharmingen | 550257 |
| CD90 | BD Pharmingen | 555596 |
| HLA-I | BD Pharmingen | 555553 |
| HLA-II | BD Pharmingen | 555558 |
| CD133 | Miltenyi Biotech | 120-001-243 |
| SSEA4 | R&D Systems | FAB1435P |
| CD105 | SantaCruz Biotech | SC-21787 |
| CD104 | BD Pharmingen | 555720 |
| CD166 | BD Pharmingen | 559263 |
| CD29 | BD Pharmingen | 555442 |
| CD24 | BD Pharmingen | 555428 |
| CD56 | AbCAM | MEM188 |
| CD138 | BD Pharmingen | 550805 |
| CD80 | BD Pharmingen | 557226 |
| CD86 | BD Pharmingen | 555659 |
| E-cadherin | BD Pharmingen | 612130 |
| IgG-FITC | BD Pharmingen | 555748 |
| IgG-PE | BD Pharmingen | 555749 |

Table 4 shows a summary of all surface marker phenotype data. All isolations tested showed positive staining for CD24, CD29, CD44, CD49c, CD73, CD90, CD166, SSEA-4 and HLA I and negative staining for CD31, CD34, CD45, CD56, CD80, CD86, CD104, CD105, CD117, CD133, CD138, CD141, E-cadherin and HLA II. In addition, all isolations analyzed were expanded for multiple generations (passage 10) and still retained their surface marker phenotype.

These cells express HLA I, but do not express HLA II, CD80 or CD86. These cell expression characteristics reflect the cell's ability to evade a host immune system. These data demonstrate that kidney-derived cells are non-immunogenic and can be administered to a patient without the need for tissue typing or immunosuppression.

In summary, these data demonstrate that kidney-derived cells from multiple donors can be isolated under various conditions (Table 1) and still maintain their surface marker phenotype. In addition, they express putative progenitor markers such as CD24 and SSEA-4, yet do not express mature, lineage-committed markers such as E-cadherin. Finally, kidney-derived cells are non-immunogenic and therefore are an attractive source of cells for use in allogeneic cell therapies.

TABLE 4

Summary of surface marker analysis.
Not determined (ND). Positive staining (+). Negative staining (−).

| Surface markers | Alternate name | Isolation | | | | | | | | | |
|---|---|---|---|---|---|---|---|---|---|---|---|
| | | 1 | 2 | 17 | 18 | 19 | 20 | 21 | 22 | 23 | 24 |
| CD29 | B1-integrin | + | + | + | + | + | + | + | + | + | + |
| CD44 | HCAM | + | + | + | + | + | + | + | + | + | + |
| CD49C | a3-integrin | ND | ND | + | + | + | + | + | + | + | + |
| CD166 | ALCAM | + | + | + | + | + | + | + | + | + | + |
| CD24 | Heat shock antigen-1 | ND | ND | + | + | + | + | + | + | + | + |
| CD73 | SH3 | ND | ND | + | + | + | + | + | + | + | + |
| CD90 | Thy-1 | ND | ND | + | + | + | + | + | + | + | + |
| SSEA4 | none | + | + | + | + | + | + | + | + | + | + |
| CD31 | PECAM-1 | − | − | − | − | − | − | − | − | − | − |
| CD34 | gp105 | − | − | − | − | − | − | − | − | − | − |
| CD45 | Ly5 | − | − | − | − | − | − | − | − | − | − |
| CD56 | NCAM | ND | ND | − | − | − | − | − | − | − | − |
| CD104 | b4-integrin | − | − | − | − | − | − | − | − | − | − |
| CD138 | Syndecan-1 | ND | ND | − | − | − | − | − | − | − | − |
| CD141 | Thrombomodulin | − | − | − | − | − | − | − | − | − | − |
| E-CADHERIN | none | − | − | − | − | − | − | − | − | − | − |
| CD105 | Endoglin | − | − | − | − | − | − | − | − | − | − |
| CD117 | c-Kit | − | − | − | − | − | − | − | − | − | − |
| CD133 | AC133 | − | − | − | − | − | − | − | − | − | − |
| CD80 | B7-1 | ND | ND | ND | ND | ND | ND | ND | − | − | − |
| CD86 | B7-2 | ND | ND | ND | ND | ND | ND | ND | − | − | − |
| HLA I | MHC-a, b, c | ND | ND | ND | ND | ND | ND | ND | + | + | + |
| HLAII | MHC-DP, DQ, DR | ND | ND | ND | ND | ND | ND | ND | − | − | − |

Example 5

Kidney-Derived Cell Gene Expression

RNA was extracted from cells from isolations 1, 2 and 17-23 using an RNA extraction kit (RNeasy Mini Kit; Qiagen, Valencia, Calif.). RNA was eluted with 50 microliters DEPC-treated water and stored at −80° C. RNA was reversed transcribed using random hexamers with the TaqMan reverse transcription reagents (Applied Biosystems, Foster City, Calif.) at 25° C. for 10 minutes, 37° C. for 60 minutes and 95° C. for 10 minutes. Samples were stored at −20° C. Using the primers described in Table 5, selected genes were investigated by conventional PCR (polymerase chain reaction). PCR was performed on cDNA samples using $RT^2$ PCR primer sets (SuperArray Biosciences Corp, Frederick Md.).

TABLE 5

Primers used in the study

| Gene | SuperArray catalogue number |
|---|---|
| Oct-4 | PPH02394A |
| Rex 1 | PPH02395A |
| Sox2 | PPH02471A |
| Human TERT (hTERT) | PPH00995A |
| FGF4 | PPH00356A |
| Pax 2 | PPH06881A |
| Cadherin-11 | PPH00667A |
| WT1 | PPH00254A |
| FOXD1 | PPH01990A |
| WNT4 | PPH02445A |
| Epo | PPH01338A |
| EpoR | PPH02642A |
| Eya1 | PPH10542A |
| HNF3B | PPH00976A |

TABLE 5-continued

Primers used in the study

| Gene | SuperArray catalogue number |
|---|---|
| Sox17 | PPH02451A |
| Gata4 | PPH010860A |
| Six2 | PPH10860A |
| CXCR4 | PPH00621A |
| BMP-2 | PPH00549A |
| BMP-7 | PPH00527A |
| GDF5 | PPH01912A |

Primers were mixed with 1 microliter of cDNA and 2× ReactionReady™ SYBR Green PCR Master Mix (SuperArray Biosciences) according to manufacturer's instructions and PCR was performed using an ABI Prism 7000 system (Applied Biosystems, Foster City, Calif.). Thermal cycle conditions were initially 50° C. for 2 min and 95° C. for 10 min followed by 34 cycles of 95° C. for 15 sec and 60° C. for 1 min. For GAPDH, PCR was performed using GAPDH primers from Applied Biosystems (cat#: 402869) 1 microliter of cDNA solution and 1× AmpliTaq Gold universal mix PCR reaction buffer (Applied Biosystems, Foster City, Calif.) according to manufacturer's instructions. Primer concentration in the final PCR reaction was 0.5 micromolar for both the forward and reverse primer and the TaqMan probe was not added. Samples were run on 2% (w/v) agarose gel and stained with ethidium bromide (Sigma, St. Louis, Mo.). Images were captured using a 667 Universal Twinpack film (VWR International, South Plainfield, N.J.) and a focal-length Polaroid™ camera (VWR International, South Plainfield, N.J.). For each gene analyzed, the final PCR product was excised from the gel and target sequence was confirmed by DNA sequencing.

RT-PCR Analysis.

All cell isolates analyzed showed a constant and stable gene expression profile. RT-PCR analysis was performed on isolations 1, 2, and 17-23 in order to detect the expression of early developmental gene marker (Oct-4, Rex-1, Sox2, FGF4, hTert), kidney developmental gene markers (Pax-2, WT-1, Eya-1, Wnt-4, BMP-7, Cadherin-11, FoxD1), metanephric mesenchymal gene markers (Pax-2, Eya-1, WT-1, Six2, and FoxD1), and genes that promote the survival of metanephric mesenchyme (BMP-7). In addition, the expression of other developmental genes, such as endodermal genes (HNF3B, CXC-R4, Sox-17, GATA-4) as well as gene markers that promote renal repair or have therapeutic value in treating kidney disease (Epo, EpoR, BMP-7, BMP-2, GDF5) were analyzed.

As shown in Table 6, all isolations showed positive expression for Oct-4 and Rex-1 and negative expression for Sox2, FGF4, hTERT and Wnt-4. Isolations 17-23 showed positive expression for Pax-2, WT1, Cadherin-11 and FoxD1. Isolations 22 and 23 showed positive expression for Eya-1, Sox-17 and CXCR-4 and negative expression for GATA-4. Isolations 17-23 expressed EpoR, but did not express Epo. Isolations 17-22 expressed BMP-2, BMP-7 and GDF5. In addition, all isolations can be expanded multiple generations (passage 10) and still retain their gene expression phenotype.

TABLE 6

Summary of gene expression analysis.
Positive expression (+). Negative expression (−). Not determined (ND).
Genes that function during early development (Early development).
Genes that function during kidney development (Kidney development).
Metanephric mesenchymal markers (Met). Endodermal lineage markers (Endoderm). Genes involved in kidney survival (renoprotective). Genes involved in metanephric mesenchyme survival (Survival).

| | | Isolation | | | | | | | | |
|---|---|---|---|---|---|---|---|---|---|---|
| Gene name | Function | 1 | 2 | 17 | 18 | 19 | 20 | 21 | 22 | 23 |
| Oct4/pfu | Early development | + | + | + | + | + | + | + | + | + |
| Rex-1 | Early development | + | + | + | + | + | + | + | + | + |
| Sox2 | Early development | − | − | − | − | − | − | − | − | − |
| FGF4 | Early development | − | − | − | − | − | − | − | − | − |
| hTert | Early development | − | − | − | − | − | − | − | − | − |
| Pax2 | Kidney development, Met | ND | ND | + | + | + | + | + | + | + |
| Cadherin-11 | Kidney development | ND | ND | + | + | + | + | + | + | + |
| FoxD1 | Kidney development, Met | ND | ND | + | + | + | + | + | + | + |
| WT-1 | Kidney development, Met | ND | ND | + | + | + | + | + | + | + |
| Eya1 | Kidney development | ND | ND | ND | ND | ND | ND | ND | + | + |
| Wnt-4 | Kidney development | ND | ND | ND | ND | ND | ND | ND | − | − |
| SIX2 | Met | ND | ND | ND | ND | ND | ND | ND | − | − |
| GATA-4 | Endoderm | ND | ND | ND | ND | ND | ND | ND | − | − |
| HNF3B | Endoderm | ND | ND | ND | ND | ND | ND | ND | + | + |
| CXC-R4 | Endoderm | ND | ND | ND | ND | ND | ND | ND | + | + |
| Sox-17 | Endoderm | ND | ND | ND | ND | ND | ND | ND | + | + |
| Epo | Renoprotective | ND | ND | − | − | − | − | − | − | − |
| EpoR | Renoprotective | ND | ND | + | + | + | + | + | + | + |
| BMP2 | Renoprotective | ND | ND | + | + | + | + | + | ND | ND |
| GDF5 | Renoprotective | ND | ND | + | + | + | + | + | ND | ND |
| BMP7 | Kidney development, Survival | ND | ND | + | + | + | + | + | ND | ND |

In summary, kidney-derived cells express genes involved in early development and kidney development. They express markers for metanephric mesenchyme and markers for renal progenitor cells. They express endodermal markers as well as factors involved in renal repair and tubulogenesis.

In total, these data demonstrate that kidney-derived cells are a source of putative renal progenitor cells that can be used for cell-based therapies to protect or repair damaged kidney tissue.

Example 6

Trophic Factor Secretion Analysis

Kidney-derived cells were shown to consistently produce trophic factors that protect and repair the kidney. Therefore, these cells may serve as a therapeutic agent for treating kidney disease.

Passage 3 cells, from isolations 17-21 were seeded at 5,000 cells/cm$^2$ in one T75 flask/isolation, each containing 15 milliliters of REGM. Cells were cultured at 37° C. in 5% carbon dioxide. After overnight culture, the medium was changed to a serum-free medium (DMEM-low glucose (Gibco), 0.1% (w/v) bovine serum albumin (Sigma), penicillin (50 units/milliliter) and streptomycin (50 micrograms/milliliter) (Gibco)) and further cultured for 8 hours. Conditioned, serum-free medium was collected at the end of incubation by centrifugation at 14,000×g for 5 min and stored at −20° C.

Cells were washed with PBS, detached using 4 milliliters TrypLE Select (Gibco) and counted with a Guava instrument (Guava Technologies, Hayward, Calif.) to estimate the number of cells in each flask. Using Searchlight Proteome Arrays (Pierce Biotechnology Inc), samples were then assayed by ELISA for the following trophic factors: tissue inhibitor of metalloproteinase-1 (TIMP-1), tissue inhibitor of metalloproteinase-2 (TIMP-2), platelet-derived epithelial growth factor bb (PDGF-bb), keratinocyte growth factor (KGF), hepatocyte growth factor (HGF), basic fibroblast growth factor (FGF2), vascular endothelial growth factor (VEGF), Heparin-binding epidermal growth factor (HB-EGF), monocyte chemotactic protein-1 (MCP-1), interleukin-6 (IL-6), interleukin-8 (IL-8), transforming growth factor alpha (TGFα), brain-derived neurotrophic factor (BDNF), stromal-derived factor 1b (SDF1b), cilliary neurotrophic factor (CNTF), basic nerve growth factor (b-NGF), neurotrophin-3 (NT-3), growth-related oncogene-alpha (GRO-α), interleukin-1b (IL-1b), interleukin-12p40 (IL-12p40), interleukin-12p70 (IL-12p70), interleukin-11 (IL-11), interleukin-15 (IL-15), matrix metalloproteinase-2 (MMP-2), matrix metalloproteinase-9 (MMP-9), angiopoietin-2 (ANG-2) and human growth hormone (HGH).

Analysis of Trophic Factor Production.

The secretion of twenty-seven different growth factors and cytokines were analyzed on isolations 17-21. The results are summarized in Table 7. All isolations secreted TIMP-1, TIMP-2, VEGF, and MMP-2 at over 300 picograms/milliliter/1×10$^6$ cells/8 hours. They secreted 50-300 picograms/milliliter/1×10$^6$ cells/8 hours of FGF2 and HGF and 1-50 picograms/milliliter/1×10$^6$ cells/8 hours of KGF, PDGF-bb, b-NGF, IL-12p40 and IL-11. SDF-1, ANG-2, HGH and Il-12p70 were not detected.

In summary, this data shows that kidney-derived cells secrete several trophic factors for protecting and repairing damaged kidney tissue. For example, FGF2, HGF, and TGFα have been implicated in renal repair. Kidney-derived cells secrete these factors at elevated and consistent levels. Therefore, these cells are a valuable source of cells for use in therapies targeting kidney diseases.

TABLE 7

SearchLight Multiplexed ELISA assay analysis of trophic factor production from kidney-derived cells. Isolation "Media only" is a control sample in serum free media alone without conditioning. Units on data shown are picograms/milliliter/1 × 10$^6$ cells/8 hours. Results shown are the average of duplicate measurements

| ISOLATION | TIMP1 | ANG2 | KGF | FGF2 | PDGF-bb | HGF | VEGF | HB-EGF | TGFa |
|---|---|---|---|---|---|---|---|---|---|
| Media only | <9.8 | <9.8 | <2.0 | <10.9 | <2 | <6.2 | <9.8 | <3.7 | <2.3 |
| 17 | 5699.4 | <9.8 | 20 | 148.4 | <2 | 91.9 | 416.3 | 46.1 | 67.7 |
| 18 | 6054.8 | <9.8 | 11.1 | 62.4 | 5.7 | 91 | 329.7 | 35.1 | 59.1 |
| 19 | 6710.6 | <9.8 | 35.1 | 160.1 | <2 | 320.9 | 580.5 | 70.2 | 119 |
| 20 | 9483.7 | <9.8 | 14.1 | 86.6 | 5 | 80.3 | 294.3 | 24.6 | 37.4 |
| 21 | 2705 | <9.8 | 13.8 | 91.5 | <2 | 162 | 298.4 | 32.4 | 34.6 |

| ISOLATION | HGH | SDF1b | BNGF | MMP9 | IL1b | MMP2 | GROa | MCP1 | IL6 |
|---|---|---|---|---|---|---|---|---|---|
| Media only | <9.8 | <50.0 | 1.2 | <39.1 | <0.4 | <62.5 | <0.8 | 2.1 | <0.8 |
| 17 | <9.8 | <50.0 | 3 | <39.1 | <0.4 | 3240 | 36.8 | 29.8 | 38.7 |
| 18 | <9.8 | <50.0 | 6.5 | 145 | 1.6 | 3487.6 | 95 | 32.7 | 40.5 |
| 19 | <9.8 | <50.0 | 20.8 | <39.1 | 3.3 | 3565.9 | 37.1 | 48.8 | 44.9 |
| 20 | <9.8 | <50.0 | 6.2 | 108 | 1.4 | 3191.3 | 499.8 | 340.9 | 80 |
| 21 | <9.8 | <50.0 | 5.8 | <39.1 | 2.2 | 2814.1 | 14.2 | 30.2 | 19.5 |

| ISOLATION | BDNF | NT3 | IL15 | TIMP2 | IL8 | IL11 | IL12p40 | IL12p70 | CNTF |
|---|---|---|---|---|---|---|---|---|---|
| Media only | <6.2 | <1.6 | <0.8 | 10 | <0.8 | <2 | <1.2 | <1.2 | 9 |
| 17 | <6.2 | <1.6 | 3.4 | 2266.2 | 31.6 | 20.5 | 14.9 | <1.2 | 30.1 |
| 18 | <6.2 | 5.4 | 2.7 | 1841.4 | 115.8 | 20.8 | 6.2 | <1.2 | <7.8 |
| 19 | <6.2 | 13 | 5.2 | 1376.7 | 36.4 | 29.3 | 21.5 | <1.2 | 93 |
| 20 | 16.2 | 12.3 | 2.3 | 1785 | 622.2 | 20.5 | 8.7 | <1.2 | 21.7 |
| 21 | <6.2 | <1.6 | 0.8 | 1193 | 12 | 19.1 | 9.3 | <1.2 | <7.8 |

Example 7

Kidney-Derived Cell Growth on Polyester Scaffolds

There is a significant need for basic materials that can be utilized for reconstructing organ tissue. Kidney-derived cells were grown on synthetic, polyester scaffolds to yield tissue-like structures that serve as the basic building block materials for kidney tissue engineering applications.

Kidney-derived cells were grown on several polyester, solvent cast films. 100 mm diameter 35/65 poly(epsilon-caprolactone-co-glycolide) (PCL/PGA) films were prepared. A 5 wt. % polymer solution was prepared by dissolving 20 g of 35/65 PCL/PGA (Ethicon, Somerville, N.J.) (inherent viscosity=1.45 deciliters/gram) in 380 g of 1,4-dioxane, anhydrous (Aldrich, Milwaukee, Wis.) at 70° C. Films were cast by pouring 3.5 milliliters of polymer solution onto 100×15 mm NALGENE polymethylpentene Petri dishes (Fisher Scientific, Pittsburgh, Pa.).

100 mm diameter 45/55 poly(epsilon-caprolactone-co-glycolide) (PCL/PGA) films were prepared. A 5 wt. % polymer solution was prepared by dissolving 20 g of 45/55 PCL/PGA (Ethicon, Somerville, N.J.) (inherent viscosity=1.88 deciliters/gram) in 380 g of 1,4-dioxane, anhydrous (Aldrich, Milwaukee, Wis.) at 70° C. Films were cast by pouring 3.5 milliliters of polymer solution onto 100×15 mm NALGENE polymethylpentene Petri dishes (Fisher Scientific, Pittsburgh, Pa.).

55 mm diameter 45/55 poly(epsilon-caprolactone-co-glycolide) (PCL/PGA) films were prepared. A 10 wt. % polymer solution was prepared by dissolving 40 g of 45/55 PCL/PGA (Ethicon, Somerville, N.J.) (inherent viscosity=1.88 deciliters/gram) in 360 g of 1,4-dioxane, anhydrous (Aldrich, Milwaukee, Wis.) at 70° C. Films were cast by pouring 5.0 milliliters or 2.5 milliliters of polymer solution onto 55×15 mm polypropylene Petri dishes (Ted Pella Inc., Redding, Calif.).

55 mm diameter 40/60 poly(epsilon-caprolactone-co-L-lactide) (PCL/PLA) films were prepared. A 10 wt. % polymer solution was prepared by dissolving 40 g of 40/60 PCL/PLA (Birmingham Polymers, Inc., Birmingham, Ala.) (inherent viscosity=1.20 deciliters/gram) in 360 g of 1,4-dioxane, anhydrous (Aldrich, Milwaukee, Wis.). Films were cast by pouring 5.0 milliliter of polymer solution onto 55×15 mm polypropylene Petri dishes (Ted Pella Inc., Redding, Calif.).

All cast films were loosely capped and placed inside a fume hood operating with a velocity flow of 100 ft/min for 4 days. Residual solvent was removed from the films by further drying in a vacuum oven (0.1-0.2 mm Hg) at 70° C. for a minimum of 4 days. After cooling to room temperature, films were sterilized by incubating in 100% ethanol overnight at room temperature. Films were then air-dried, washed with PBS and cells from isolations 17 or 18 were seeded onto the films at 5000 cells/cm$^2$ in REGM and cultured at 37 C for 4-9 days.

Analysis of Kidney-derived Cell Growth on Polyester Scaffolds.

Isolations 17 or 18 were cultured in REGM on various solvent-cast polyester films, as summarized on Table 8. In each case, PCL/PGA-based scaffolds supported the growth of an intact cell monolayer. In addition, the cell/film combination constructs were lifted from the casting dish, while maintaining a cell monolayer structure. These kidney-derived cell/film constructs can be used as cell sheet materials in tissue engineering applications.

TABLE 8

Summary of kidney-derived cells tested on different films.

| ISOLATION | SCAFFOLD |
|---|---|
| Isolation 17 | 35/65 PCL/PGA |
| Isolation 18 | 45/55 PCL/PGA |
| Isolation 18 | 60/40 PCL/PLA |
| Isolation 18 | 45/55 PCL/PGA |
| Isolation 18 | 35/65 PCL/PGA |

Example 8

Kidney-Derived Cell Tubulogenesis In Vitro

Kidney-derived cells can be thawed at passage 4 and passage 10 and then triturated into a single-cell suspension at 4×10$^4$ cells/milliliter in a type I collagen solution containing 66% vitrogen 100 (3 milligrams/milliliter (Cohesion Technologies, Palo Alto, Calif.). Cells in suspension can be plated onto a de-cellularized omentum membrane. The collagen/cell mixture can then be incubated for 30 minutes at 37° C., 5% $CO_2$, 95% air to allow the collagen to gel and then culture medium is added. Cells are fed every 3 days for 7 days. On day 7, cultures are treated with varying concentrations of hepatocyte growth factor and further cultured until tubulogenesis is observed.

These observations demonstrate that kidney-derived cells can self-organize into tubule structures in vitro. These structures have value as building blocks for kidney reconstruction applications as well as for developing drug screening and toxicology assays.

Example 9

Kidney-Derived Cells for Drug Screening and Toxicology Assay

Human kidney-derived cells offer new opportunities for in vitro discovery and safety assessment of novel therapeutic molecules. Tubules derived from kidney-derived cells enable the development of a nephrotoxic as well as nephrogenic model system for the discovery of novel kidney regenerative or renoprotective drugs. This kidney-derived cell drug discovery and toxicology assay platform system will enhance research and development of new compounds for the treatment of kidney disease.

Kidney-derived cells can be plated at 5,000 cells/cm$^2$ into wells of a 96 well plate using the methods described in Example 8. These plates serve as the assay system for testing various compounds and small molecules for their ability to enhance or prevent tubule formation. To determine the effects of the various compounds, individual wells are analyzed by light microscopy for tubulogenesis and the formation of branching networks of tubules. In addition, RT-PCR can be conducted on cells in each individual well using methods described in Example 5.

Kidney-derived cells can be cultured in a 96 well format and tubulogenesis can be modulated by the addition of various compounds and small molecule drugs. Different growth factors and drugs may induce kidney-derived cell tubulogenesis and branching as well as increase gene expression of BMP-7, BMP-2, GDF5, BMP receptor-1 and BMP receptor-2. An up-regulation of these genes correlates with increased tubule formation. An increase in BMP-7 also suggests that the test drug will promote renal repair by increasing BMP-7 in the damaged kidney. Likewise, a down-regulation or absence of gene expression correlates with inhibition of tubulogenesis or cytotoxicity as well as a decreased ability for the test drug to stimulate kidney repair.

In summary, exploitation of kidney-derived cells ability to form tubules as well as the expression of BMP molecules and their receptors, offers the opportunity to develop a novel drug discovery and toxicology assay platform system. This assay system will enhance the research and development of new compounds for the treatment of kidney disease.

Example 10

Kidney-Derived Cell Multipotentiality

Kidney-derived cells are a potential source of progenitor cells, capable of differentiation into adipocytes and osteoblasts. This data demonstrates the multipotential nature of kidney-derived cells and further illustrates their characteristics as a progenitor cell.

For differentiation assays, kidney-derived cells can be cultured in REGM in 5% $CO_2$ at 37° C. medium for 1 week before being changed to adipogenic (DMEM/F12, 3% FCS, 33 micromolar biotin, 17 micromolar pantothenate, 100 nanomolar insulin, 1 micromolar dexamethasone, 0.25 microgram/milliliter amphotericin B, and 0.25 millimolar IBMX) or osteogenic (DMEM, 10% FCS, 0.2 millimolar ascorbic acid, 25 millimolar β-glycerophosphate, 500 nanomolar dexamethasone, and 20 nanomolar glutamine) differentiation medium. Cells can be cultured for an additional 3 weeks with medium exchange every second day, then fixed for 10 minutes in 4% paraformadehyde. Adipocytes are identified by staining with Nile Red (Molecular Probes; 1:2000 in PBS) for 15 min Osteoblasts are identified by alkaline phosphatase assay using 0.1 milligrams/milliliter Fast Blue BB salt (Sigma), 0.1 milligrams/milliliter Naphthol AS-MX phosphate (Sigma), and 2 millimolar $MgCl_2$ in 0.1 molar Tris-HCl (pH 8.5). Images are captured with a Nikon digital camera connected to a Nikon TS 100 ECLIPSE inverted microscope. 10T1/2 cells were used as a positive control in differentiation assays.

After three weeks in adipogenic medium, adipocytes can be identified by the accumulation of Nile Red stained lipid droplets within the cytoplasmic compartment of the kidney-derived cells. After three weeks in osteogenic medium, osteoblasts can be identified by an increase in alkaline phosphatase activity as compared to kidney-derived cells growth in REGM only.

In summary, this data further shows that kidney-derived cells are potential progenitor cells, capable of differentiation into at least two distinct cell lineages, adipocytes and osteoblasts. These cells are therefore a source of cells for renal regeneration and cell therapy applications.

Example 11

Kidney-Derived Cell Tubulogenesis In Vivo

Three 35/65 PCL/PGA (10 cm diameter×2 mm thickness) films were seeded with human kidney-derived cells (10,000 cells/cm²) and cultured in REGM (Cambrex) at 37° C. and 5% carbon dioxide for 8 days (as described in Example 7). The 35/65 PCL/PGA foam scaffold was prepared according to the methods described in U.S. Pat. No. 6,355,699, incorporated herein by reference in its entirety. The cell/film constructs were then removed from the film-casting dish, stacked into three layers and applied to a 35/65 PCL/PGA foam scaffold support. This construct was then cultured for an additional 24 hours and then cut into 3×3 mm square pieces prior to implantation. The implants were then washed with PBS and transferred to a 6-well plate filled with PBS for transport.

The implants were subcutaneously implanted bilaterally in the dorsal lateral thoracic-lumbar region of SCID mice. Male SCID mice (Fox Chase SCID CB17SC strain) were purchased from Taconic Inc., (Hudson, N.Y.). and were 5 weeks old. Two implants were placed in each SCID mouse. Two skin incisions, each approximately 5 mm in length, were made on the dorsum of the mice. The incisions were placed transversely over the lumbar area about 5 mm cranial to the palpated iliac crest, with one on either side of the midline. The skin was then separated from the underlying connective tissue to make a small pocket, and the implant was placed about 10 mm cranial to the incision. The skin incisions were closed with Reflex 7 metal wound clips. After 3 weeks, the implants were removed from the subcutaneous pocket, fixed in 10% formalin, embedded in paraffin wax, sectioned, stained with hematoxylin and eosin (H&E) and evaluated by a pathologist using light microscopy techniques.

Kidney-derived cells formed tubule-like structures within the layers of PCL/PGA film. These tubules showed a distinct epithelial wall and a clear lumen. Kidney-derived cells infiltrated the foam scaffold, deposited extracellular matrix, and formed a dense, tissue-like structure. In addition, kidney-derived cells within the foam stimulated angiogenesis and the formation of vascular networks.

In summary, human kidney-specific cells formed tubule structures after exposure to an in vivo microenvironment. The ability of kidney-derived cells to respond to microenvironmental signals and to instruct the cells to form tubules, further illustrates the renal progenitor nature of these cells. In addition, the cells migrated into the foam scaffolds, forming a tissue-like structure that promoted angiogenesis. This data illustrates the utility of kidney-derived cells as cellular building blocks for reconstructing kidney tubules and ultimately for use in kidney tissue engineering applications.

Example 12

Kidney-Derived Cells are Renoprotective in Animal Models of Renal Disease

Kidney-derived cells secrete several trophic factors that have been implicated in renal repair and regeneration (see Example 6). Therefore, when kidney-derived cells are administered to an animal that has sustained renal injury, the cells will produce trophic factors that protect and repair the damaged kidney. Kidney-derived cells will be tested for renoprotection in three different animal models of renal failure, drug induced injury, ischemia-reflow injury and ureter obstruction induced injury.

Induction of Renal Failure

Ischemia/reflow injury will be induced as follows. Mice will be placed in a clean cage with sufficient water. The surgical area will be prepared by clipping the hair. Mice (six to eight week old C57BL/6J mice will be purchased from The Jackson Laboratory, Bar Harbor, Me.) will be anesthetized by injecting ketamine (100 milligrams/kilogram) and xylazine (milligrams/kilogram) via intraperitoneal injection. The level of anesthesia will be assessed by the lack of toe-pinch-reflex.

Anesthetized mice will be placed on their dorsal side and the ventral side disinfected with betadine. A small midline incision will be made, first in the skin and then in the peritoneal muscle. The intestines will be gently moved aside, the kidneys will be exposed and the renal arteries identified. Both renal arteries will be clamped for 25 or 30 minutes using vascular clamps. During this time, the mouse will be kept warm using water circulating heating pads. Also, the exposed area will be kept warm with a sterile warm saline and sterile gauze pieces soaked in warm saline. Thirty minutes later, the clamps will be removed, the peritoneal wall sutured with one or two discontinuous sutures and the skin will be closed with wound clips. Drug induced renal failure will be performed in mice using a single subcutaneous injection of cisplatin (5 or 10 milligrams/kilogram).

Ureter obstruction induced renal failure will be generated in mice as follows. The mice will be anesthetized with isofluorane (1-3%). The abdomen will be shaved and washed with 70% alcohol followed by betadine. A 2-centimeter midline abdominal incision will be made and the abdominal wall opened. The left kidney and the ureter will be dissected free of fat. Two 8-0 non-absorbable ties will be placed on the ureter which is then transected between the ligatures. The intestines will be returned to the abdomen and the muscle layer closed with 4-0 Dexon and the skin closed with staples.

Cell Transplantation

At the time of cell injection, kidney-derived cells will be thawed at 37° C. (water bath) and washed two times in PBS and resuspended in 1 milliliter of PBS. Cells will be counted using a hemocytometer. Cell viability will be determined by trypan blue dye exclusion. Cells must have a viability of 75% or greater at the time of injection. If viability is less than 75%, then cells will be discarded. Cells will be reconstituted at a concentration of $0.5\times10^6$ cells/300 microliter PBS or $0.1\times10^6$ cells/300 microliter PBS. Cells suspended in PBS (carrier vehicle) will be injected into the anterior facial vein using a 1 milliliter syringe fitted with a 26 gauge needle. For ischemia/reflow studies and ureter obstruction induced injury studies, ten mice per treatment group will be injected with cells or PBS two hours after injury. For the drug induced renal failure studies, all animals will receive cells or PBS twenty-four hours after injury.

Blood samples (50 microliters) will be collected from the tail vein prior to induction of renal failure and on days 2, 5, and 7. Serum creatinine will be analyzed using HPLC detection. Blood-urea-nitrogen (BUN) levels will be measured using a detection kit from Roche Diagnostics Systems (Branchburg, N.J.).

Due to the secretion of renoprotective trophic factors, kidney-derived cells may prevent renal damage in animal models of renal failure.

Example 13

Evaluation of the Renoprotective Efficacy of Human Kidney-Derived Cells in a Rodent Model of Obstructive Nephropathy Disease The purpose of the pilot study was to evaluate the renoprotective effects of human kidney derived cells (hKDC) in a unilateral ureter obstruction (UUO) model of renal injury. The UUO model is an effective model for short-term, obstructive nephropathy and tubulointerstitial fibrosis. To evaluate renoprotective efficacy, cell biodistribution, blood-urea-nitrogen (BUN), serum creatinine (SCr) and histological injury were assessed in injured mice twelve days post cell transplantation. In this report, data shows that at the time of necropsy, hKDC were present in both injured and non-injured kidneys. Histological assessment demonstrated that the administration of $0.2\times10^6$ hKDC caused a measurable reduction in the overall extent of ureter obstruction induced tubular injury.

Despite the many different etiologies of chronic kidney disease (CKD), inflammation within the tubulointerstitial space, leading to fibrosis, is a histological hallmark of chronic renal failure. Although widespread use of angiotensin-converting enzyme inhibitors and angiotensin receptor blockers for CKD represents a remarkable medical success, these drugs seldom halt renal fibrosis. Therefore, developing new strategies that prevent or inhibit interstitial fibrinogenesis is an important goal for improving the current standard of care. Despite efforts focused on developing pharmacological and small-molecule based therapies, investigations into a cell therapy-based approach are limited.

Recent studies have demonstrated that bone marrow derived mesenchymal stem cells (MSCs) are renotropic and help repair the kidneys after drug and ischemia-reperfusion induced injury. Morigi et al., Mesenchymal stem cells are renotropic, helping to repair the kidney and improve function in acute renal failure. *J Am Soc Nephrol.* 2004 July; 15(7): 1794-804; Klahr and Morrissey. Obstructive nephropathy and renal fibrosis. *Am. J Renal Physiol.* 2002 November; 283(5): F861-75. 2002. It was also shown that MSCs could prevent glycerol-induced acute renal failure. Herrera et al, Mesenchymal stem cells contribute to the renal repair of acute tubular epithelial injury. *Int. J Mol Med.* 2004 December; 14(6): 1035-41. Interestingly, these MSC-mediated, protective effects might not act through stem cell differentiation mechanisms, but rather through the secretion of important trophic factors that prevent cellular injury and promote epithelial and endothelial repair.

MSCs have indeed improved the outcome of acute renal injury in several animal models, but whether MSCs can delay renal failure in chronic kidney disease is yet to be determined Studies have recently shown that transplanted MSCs could prevent the loss of peritubular capillaries, as well as reduce markers of renal fibrosis in a mouse model of Alport disease. Ninichuk et al., Multipotent mesenchymal stem cells reduce interstitial fibrosis but do not delay progression of chronic kidney disease in collagen4A3-deficient mice. *Kidney Int.* 2006 July; 70(1):121-9. Unfortunately, this study also shows that transplanted MSCs were unable to promote animal survival or even delay the onset of renal failure.

In the current study, the renoprotective and anti-fibrotic effects of hKDC in the mouse UUO model was investigated. The UUO model of obstructive nephropathy has proven to be a valuable tool for studying the molecular and cellular changes that occur within the interstitium of the kidney. This model has also shown utility in determining the efficacy of treatments aimed at halting, or even reversing fibrosis, and ultimately the progression of many chronic renal diseases.

Methods

Animal model. Thirteen, female C57BL/6J mice (The Jackson Laboratory, Bar Harbor, Me.) were anesthetized with 1-3% Isofluorane. The abdomen of each animal was shaved and cleaned with 70% alcohol, followed by betadine. A midline, abdominal incision was made. The abdominal wall was opened and the intestines were moved out onto the chest and protected with wet gauze. The left kidney was located and the ureter dissected free of fat. Two, 8-0 non-absorbable ties were placed on the ureter. For the sham treatment group, no ties were used. The intestines were returned to the abdomen and one cubic centimeter of warm saline was placed into the peritoneal cavity. The muscle layer was then closed with 4-0 Dexon and the skin closed with staples. Isoflurane was discontinued and the mice were allowed to recover with 100% oxygen on a heating pad until ambulatory.

Cell Preparation. hKDC, lot number 032906, passage 6 were isolated and expanded as described in Example 1 and CBAT invention report, "Isolation of Human Kidney Derived Cells (Study 2)", Mar. 29, 2006, David Colter, Agnes Seyda, Charito Buensuceso, Walter Laredo). HUTC (lot#2512380, passage 6) was obtained from the Stem Cell Internal Venture (Radnor, Pa.).

Cell Transplantation Immediately after animals recovered from surgery, HUTC and passage 10 hKDCs were thawed at 37° C., washed two times in Hanks Balanced Salt Solution w/o $Ca^{++}/Mg^{++}$ (HBSS) and resuspended in one milliliter of HBSS. Cells were then counted using a hemocytometer and cell viability was determined by trypan blue dye exclusion. Cells were reconstituted at a concentration of $1.0 \times 10^6$ viable cells/milliliter in HBSS. Cells suspended in 200 microliters of HBSS were then transplanted, via tail vein injection, using a one-milliliter syringe fitted with a 27-gauge needle.

TABLE 9

Experimental design. Sham animals underwent surgical procedures. However, the ureter was not obstructed.

| Treatment group | Number of animals | Gender | Test material | Cell dose |
|---|---|---|---|---|
| 1 | 3 | Female | Sham | NA |
| 2 | 5 | Female | HUTC | $0.2 \times 10^6$ |
| 3 | 5 | Female | hKDC | $0.2 \times 10^6$ |

Biodistribution. All animals were sacrificed on day 12 post cell transplantation by carbon dioxide asphyxiation. Kidneys, lungs, brain and heart were removed from each animal. Half of each kidney was then fixed in 10% neutral buffered formalin for histological analysis. The remaining kidney half, and all other organs were snap frozen in liquid nitrogen. All frozen organs were then homogenized using an Omni TH homogenizer fitted with a 7 mm disposable rotor stator generator probe (Omni International, Inc., Marietta, Ga.). Total RNA was then extracted using an RNeasy Plus Mini Kit (Qiagen, Valencia, Calif.). RNA was eluted with 50 μL DEPC-treated water and quantified using a NanoDrop 1000 (NanoDrop Technologies, Wilmington, Del.). RNA was then reverse transcribed using random hexamers and Taqman reverse transcription reagents (Applied Biosystems, Foster City, Calif.). PCR reactions were then performed on cDNA samples using human specific β2 microglobulin primer probes (catalogue number 4310886E, Applied Biosystems, Foster City, Calif.). PCR was then performed using an ABI Prism 7900 HT Sequence Detection System (Applied Biosystems, Foster City, Calif.).

Serum chemistry analysis. At the time of necropsy, whole blood was collected, allowed to clot, placed into microcentrifuge tubes, and centrifuged at 2500 rpm for 15 minutes to separate serum from other blood components. Serum samples were then analyzed using a VetAce Chemistry Analyzer (Alpha Wassermann Diagnostic Technologies, LLC, West Caldwell, N.J.).

Histology evaluation. Fixed kidney tissue was embedded in paraffin wax, sectioned (5 μm-thick) and stained with hematoxylin/eosin (H&E) and Masson's Trichrome. The sections were then scored for tubular injury (tubular necrosis, dilation, interstitial cellular infiltrate) and interstitial fibrosis (collagen deposition) using a scoring index ranging from 1 to 4 (1=minimal, 2=mild, 3=moderate, 4=severe). The evaluator was blinded to the treatment group assignments.

Results

Biodistribution. To evaluate the organ biodistribution of transplanted cells, an RT-PCR based method was utilized. A real-time PCR primer/probe specific to human β2 microglobulin RNA transcripts was utilized. As shown in Table 10 and Table 11, both HUTC and hKDCs could be detected in many, but not all of the animals. Sham treatment served as an effective negative control due to that fact that no human cells were transplanted into these animals. As shown in Table 10, heart from animal 1 showed Ct values in all three replicate measurements. The mean Ct value for this sample was 36.5. Therefore, positive signal is determined when all three replicate measurements shown in Table 10 have a positive Ct value, and the mean Ct value is <36.5. Due to the fact that animal 1 did not receive human cells, a Ct value of 36.5 or greater indicates that no human cells are detected. As shown in Table 11, no tissues from sham treated animals showed human cell transcripts. However, HUTC was detected in organs from 2 out of the 5 animals tested. The cells were detected in the lungs, injured kidney and uninjured kidney from animal 7 and uninjured kidney, brain and lungs from animal 8. hKDCs were detected in 3 out of the 5 animals tested. The cells were detected in the injured kidney, uninjured kidney, heart, brain and lungs of animal 11. They were also detected in the injured kidney, uninjured kidney, and heart of animal 12. hKDCs were also detected in the uninjured kidney, heart and lungs of animal 13.

Serum Chemistry To assess renal function, BUN and SCr was measured. In the unilateral obstruction model, one of the two kidneys remains uninjured. The animal is therefore able to compensate for any loss of renal function sustained by the injured kidney. Because of the remaining uninjured kidney, BUN and SCr are expected to be within the normal range. As shown in Table 12, the serum levels of both BUN and SCr remain unchanged between all treatment groups. Sham treatment showed a mean BUN measurement of 20.7+/−3.2 mg/dL and SCr of 0.4+/−0.06 mg//dL. HUTC treatment resulted in a mean BUN measurement of 25.6+/−5.0 mg/dL and SCr of 0.4+/−0.07. hKDC treatment resulted in a mean BUN measurement of 26.0+/−4.7 mg/dL and SCr of 0.4+/−0.04 mg/dL.

Histology Tubular injury and degree of interstitial fibrosis was qualitatively measured in histological sections from sham, HUTC and hKDC treated animals. As shown in Table 12, sham treatment resulted in minimal tubular injury, with a score of 1.0 in all three animals evaluated. HUTC treatment resulted in minimal tubular repair, with a mean injury score of 4.0 However, as compared to HUTC treatment, hKDC treatment resulted in a reduction in the overall extent of tubular injury, with all five animals demonstrating an injury score of 3.0. With regards to fibrotic changes, sham treated animals showed a minimal degree of collagen deposition within the interstitium of the kidneys and therefore minimal fibrosis (mean score=1.0). However, HUTC and hKDC treatment showed evidence of mild fibrosis, with mean scores of 2.4 and 2.0, respectively.

In this report, the renoprotective and anti-fibrotic effects of hKDC are described. Data shows that transplanted human cells reside in both injured and non-injured kidneys twelve days post transplantation. hKDC treatment caused a measurable reduction in the overall degree of tubular injury as compared to hUTC treatment. Therefore, this pilot study indicates that hKDC elicits renoprotective effects in the UUO model of obstructive nephropathy.

TABLE 10

Biodistribution. Organ tissue was evaluated by RT-PCR for the presence of human β2 microglobulin RNA transcripts. Analysis was conducted three times for each tissue. Refer to Table 9 for treatment group assignments. "Ct", cycle threshold. "nd", not detected. "Kidney (I)", injured kidney. Data shown here is summarized in Table 11.

| Treatment Group 1 | | | Treatment Group 2 | | | Treatment Group 3 | | |
|---|---|---|---|---|---|---|---|---|
| Animal | Tissue | Ct | Animal | Tissue | Ct | Animal | Tissue | Ct |
| 1 | Heart | 35.78 | 4 | Kidney (I) | 37.86 | 9 | Kidney (I) | nd |
| 1 | Heart | 37.20 | 4 | Kidney (I) | nd | 9 | Kidney (I) | nd |
| 1 | Heart | 36.40 | 4 | Kidney (I) | nd | 9 | Kidney (I) | nd |
| 1 | Brain | nd | 4 | Heart | nd | 9 | Heart | nd |
| 1 | Brain | nd | 4 | Heart | nd | 9 | Heart | nd |
| 1 | Brain | 39.13 | 4 | Heart | nd | 9 | Heart | nd |
| 1 | Lungs | nd | 4 | Brain | nd | 9 | Brain | 37.37 |
| 1 | Lungs | 37.76 | 4 | Brain | nd | 9 | Brain | nd |
| 1 | Lungs | nd | 4 | Brain | nd | 9 | Brain | nd |
| 2 | Heart | nd | 4 | Lungs | nd | 9 | Lungs | nd |
| 2 | Heart | nd | 4 | Lungs | 35.84 | 9 | Lungs | nd |
| 2 | Heart | nd | 4 | Lungs | nd | 9 | Lungs | nd |
| 2 | Brain | nd | 5 | Kidney (I) | nd | 10 | Kidney (I) | nd |
| 2 | Brain | nd | 5 | Kidney (I) | nd | 10 | Kidney (I) | 37.36 |
| 2 | Brain | nd | 5 | Kidney (I) | nd | 10 | Kidney (I) | nd |
| 2 | Lungs | nd | 5 | Heart | nd | 10 | Heart | nd |
| 2 | Lungs | nd | 5 | Heart | nd | 10 | Heart | nd |
| 2 | Lungs | nd | 5 | Heart | nd | 10 | Heart | nd |
| 3 | Heart | 38.72 | 5 | Brain | nd | 10 | Brain | nd |
| 3 | Heart | nd | 5 | Brain | 32.80 | 10 | Brain | nd |
| 3 | Heart | nd | 5 | Brain | nd | 10 | Brain | nd |
| 3 | Brain | nd | 5 | Lungs | nd | 11 | Kidney (I) | 36.48 |
| 3 | Brain | nd | 5 | Lungs | nd | 11 | Kidney (I) | 38.58 |
| 3 | Brain | nd | 5 | Lungs | nd | 11 | Kidney (I) | 35.72 |
| 3 | Lungs | nd | 6 | Kidney (I) | nd | 11 | Kidney | 32.57 |
| 3 | Lungs | nd | 6 | Kidney (I) | nd | 11 | Kidney | 32.22 |
| 3 | Lungs | nd | 6 | Kidney (I) | nd | 11 | Kidney | 31.61 |
| | | | 6 | Heart | nd | 11 | Heart | 33.55 |
| | | | 6 | Heart | nd | 11 | Heart | 34.21 |
| | | | 6 | Heart | nd | 11 | Heart | 32.91 |
| | | | 6 | Brain | nd | 11 | Brain | 35.33 |
| | | | 6 | Brain | nd | 11 | Brain | 34.94 |
| | | | 6 | Brain | 37.62 | 11 | Brain | 35.28 |
| | | | 6 | Lungs | nd | 11 | Lungs | 33.73 |
| | | | 6 | Lungs | nd | 11 | Lungs | 34.01 |
| | | | 6 | Lungs | nd | 11 | Lungs | 33.99 |
| | | | 7 | Kidney (I) | 33.41 | 12 | Kidney (I) | 34.62 |
| | | | 7 | Kidney (I) | 33.12 | 12 | Kidney (I) | 34.84 |
| | | | 7 | Kidney (I) | 33.45 | 12 | Kidney (I) | 34.51 |
| | | | 7 | Kidney | 34.07 | 12 | Kidney | 34.94 |
| | | | 7 | Kidney | 33.78 | 12 | Kidney | 35.55 |
| | | | 7 | Kidney | 33.81 | 12 | Kidney | 34.32 |
| | | | 7 | Heart | nd | 12 | Heart | 34.52 |
| | | | 7 | Heart | 38.79 | 12 | Heart | 34.71 |
| | | | 7 | Heart | 39.97 | 12 | Heart | 34.38 |
| | | | 7 | Brain | nd | 12 | Brain | 25.19 |
| | | | 7 | Brain | nd | 12 | Brain | nd |
| | | | 7 | Brain | nd | 12 | Brain | nd |
| | | | 7 | Lungs | 31.69 | 12 | Lungs | nd |
| | | | 7 | Lungs | 31.84 | 12 | Lungs | nd |
| | | | 7 | Lungs | 31.92 | 12 | Lungs | 39.21 |
| | | | 8 | Kidney (I) | nd | 13 | Kidney (I) | nd |
| | | | 8 | Kidney (I) | nd | 13 | Kidney (I) | 38.66 |
| | | | 8 | Kidney (I) | nd | 13 | Kidney (I) | nd |
| | | | 8 | Kidney | 34.16 | 13 | Kidney | 33.52 |
| | | | 8 | Kidney | 34.61 | 13 | Kidney | 33.36 |
| | | | 8 | Kidney | 34.08 | 13 | Kidney | 32.69 |
| | | | 8 | Heart | nd | 13 | Heart | 34.76 |
| | | | 8 | Heart | nd | 13 | Heart | 34.55 |
| | | | 8 | Heart | nd | 13 | Heart | 34.28 |
| | | | 8 | Brain | 31.59 | 13 | Brain | nd |
| | | | 8 | Brain | 31.73 | 13 | Brain | 38.78 |
| | | | 8 | Brain | 31.76 | 13 | Brain | 38.01 |
| | | | 8 | Lungs | 32.64 | 13 | Lungs | 33.52 |
| | | | 8 | Lungs | 32.96 | 13 | Lungs | 33.79 |
| | | | 8 | Lungs | 33.44 | 13 | Lungs | 34.11 |

TABLE 11

Biodistribution summary. Data shown describes the number of animals positive for human cells/total number of animals tested. Positive signal is determined when all three replicate measurements shown in Table 10 have a positive Ct value and the mean Ct value is <36.5. Refer to Table 9 for treatment group assignments. "nd" not determined. "Kidney (I)", injured kidney.

|  | Group 1 | Group 2 | Group 3 |
|---|---|---|---|
| Kidney (I) | nd | 1/5 | 2/5 |
| Kidney | nd | 1/5 | 3/5 |
| Heart | 0/3 | 0/5 | 3/5 |
| Brain | 0/3 | 1/5 | 1/5 |
| Lungs | 0/3 | 1/5 | 2/5 |

TABLE 12

Serum chemistry. Refer to Table 9 for treatment group assignments SEM, standard error of the mean.

| Treatment | Animal number | BUN (mg/dL) | Creatinine (mg/dL) |
|---|---|---|---|
| 1 | 1 | 22 | 0.4 |
|  | 2 | 23 | 0.4 |
|  | 3 | 17 | 0.3 |
|  | Mean: 20.7 | Mean: 0.4 | |
|  | SEM: 3.2 | SEM: 0.06 | |
| 2 | 4 | 24 | 0.4 |
|  | 5 | 21 | 0.5 |
|  | 6 | 26 | 0.4 |
|  | 7 | 23 | 0.4 |
|  | 8 | 34 | 0.3 |
|  | Mean: 25.6 | Mean: 0.4 | |
|  | SEM: 5.0 | SEM: 0.07 | |
| 3 | 9 | 33 | 0.5 |
|  | 10 | 24 | 0.4 |
|  | 11 | 20 | 0.4 |
|  | 12 | 26 | 0.4 |
|  | 13 | 27 | 0.4 |
|  | Mean: 26.0 | Mean: 0.4 | |
|  | SEM: 4.7 | SEM: 0.04 | |

TABLE 13

Histology. The degree of renal tubular injury (tubular necrosis, dilation and interstitial cellular infiltrate) and fibrosis (collagen deposition) was scored, in a blinded fashion, using a scoring index ranging from 1 to 4 (1 = minimal, 2 = mild, 3 = moderate, 4 = severe).

| Animal | Fibrosis | Tubular injury |
|---|---|---|
| Treatment group 1 | | |
| 1 | 1 | 1 |
| 2 | 1 | 1 |
| 3 | 1 | 1 |
| Mean: 1.0 | Mean: 1.0 | |
| Treatment group 2 | | |
| 4 | 2 | 4 |
| 5 | 2 | 4 |
| 6 | 2 | 4 |
| 7 | 3 | 4 |
| 8 | 3 | 4 |
| Mean: 2.4 | Mean: 4.0 | |
| Treatment group 3 | | |
| 9 | 2 | 3 |
| 10 | 2 | 3 |
| 11 | 2 | 3 |
| 12 | 2 | 3 |
| 13 | 2 | 3 |
| Mean: 2.0 | Mean: 3.0 | |

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed:

1. A method for treating ischemic kidney disease in a human or an immunocompromised mouse comprising administering directly to the kidney a therapeutically effective amount of an isolated or purified human kidney-derived cell population,
    wherein said cell population is capable of self-renewal and expansion in culture, wherein the cell population is positive for expression of HLA-I and CD44 and at least one of Oct-4, Rex-1, Pax-2, Cadherin-11, FoxD1, WT1, Eya1, HNF3B, CXC-R4, Sox-17, EpoR, BMP2, BMP7, and GDF5, and negative for the expression of CD133, E-cadherin, and Wnt-4 and at least one of Sox2, FGF4, hTert, SIX2 and GATA-4, and
    wherein said administration reduces or eliminates the ischemic kidney disease in the treated human or immunocompromised mouse.

2. The method of claim 1, wherein the administration of said cell population induces an effect selected from: (a) formation of blood vessels supplying blood to the ischemic tissue; (b) blood flow to the ischemic tissue; (c) oxygen supply to the ischemic tissue; and (d) combinations thereof.

3. The method of claim 1, wherein the administration of said cell population induces formation of kidney subcapsular region tissue, kidney cortex tissue, or kidney medulla tissue.

4. The method of claim 1, wherein the treating ischemic kidney disease is in a human.

5. The method of claim 1, wherein the human kidney-derived cell population is positive for expression of at least one of Eya1, WT1, FoxD1, BMP7, BMP2, GDF5, EpoR and Rex-1, and negative for expression of at least one of Sox2, FGF4, and hTert.

6. The method of claim 1, wherein the human kidney-derived cell population is positive for at least one of cell-surface markers, CD24, CD29, CD49c, CD73, CD90, CD166, and SSEA-4, and negative for at least one of cell-surface markers HLA II, CD31, CD34, CD45, CD56, CD80, CD86, CD104, CD105, CD117, CD138, and CD141.

7. The method of claim 1, wherein the human kidney-derived cell population is positive for at least one of the surface markers CD166 and SSEA-4, and negative for at least one of the cell-surface markers HLA II, CD80, CD86, CD133, CD141 and E-cadherin.

8. The method of claim 1, wherein the human kidney-derived cell population is positive for the cell-surface marker HLA I, and negative for at least one of cell-surface markers HLA II, CD80, and CD86.

9. The method of claim 1, wherein the human kidney-derived cell population is non-immunogenic for allogeneic transplantation in a human subject.

10. The method of claim 1, wherein the human kidney-derived cell population is derived from kidney cortex, kidney medulla or kidney subcapsular region.

11. The method of claim 1, wherein the method comprises administering a pharmaceutical composition comprising the isolated or purified human kidney-derived cell population.

\* \* \* \* \*